(12) United States Patent
Dejima

(10) Patent No.: US 10,433,712 B2
(45) Date of Patent: Oct. 8, 2019

(54) SHEATHING TUBE AND ENDOSCOPIC SURGICAL DEVICE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 253 days.

(21) Appl. No.: 15/275,472

(22) Filed: Sep. 26, 2016

(65) Prior Publication Data

US 2017/0007101 A1    Jan. 12, 2017

Related U.S. Application Data

(63) Continuation of application No. PCT/JP2015/059355, filed on Mar. 26, 2015.

(Continued)

(51) Int. Cl.
| | | |
|---|---|---|
| *A61B 1/00* | (2006.01) | |
| *A61B 17/34* | (2006.01) | |
| *A61B 1/313* | (2006.01) | |
| *A61B 17/29* | (2006.01) | |

(52) U.S. Cl.
CPC ........ *A61B 1/00135* (2013.01); *A61B 1/0005* (2013.01); *A61B 1/00154* (2013.01);
(Continued)

(58) Field of Classification Search
CPC ............ A61B 1/00135; A61B 17/3421; A61B 17/3462; A61B 2017/247; A61B 1/00154; A61B 1/018
(Continued)

(56) References Cited

U.S. PATENT DOCUMENTS

| | | |
|---|---|---|
| 3,789,852 A | 2/1974 | Kim et al. |
| 4,586,491 A * | 5/1986 | Carpenter .............. A61B 1/018 600/106 |

(Continued)

FOREIGN PATENT DOCUMENTS

| | | |
|---|---|---|
| EP | 1634544 | 3/2006 |
| JP | 2004-180858 | 7/2004 |

(Continued)

OTHER PUBLICATIONS

"Written Opinion of the International Searching Authority (Form PCT/ISA/237)" of PCT/JP2015/059355, dated Jun. 9, 2015, with English translation thereof, pp. 1-6.

(Continued)

*Primary Examiner* — Aaron B Fairchild
(74) *Attorney, Agent, or Firm* — JCIPRNET

(57) ABSTRACT

An outer port sheathing an overtube, includes: a first cylindrical member having a distal end opening from which the overtube is delivered; a second cylindrical member that is rotatably connected to the first cylindrical member and has a base end opening into which the overtube is introduced; rotation restriction means that restricts rotation of the overtube with respect to the second cylindrical member; a spring member that is deformable between a rotation locked state where rotation of the second cylindrical member with respect to the first cylindrical member is restricted by engagement of the spring member with the first cylindrical member, and a rotation unlocked state where the engagement is released and the rotation is allowed; and a rotation operating member that is rotatable in an axial direction of the second cylindrical member and deforms the spring member between the rotation locked state and the rotation unlocked state.

4 Claims, 22 Drawing Sheets

Related U.S. Application Data

(60) Provisional application No. 61/971,272, filed on Mar. 27, 2014.

(52) U.S. Cl.
CPC ...... *A61B 17/3421* (2013.01); *A61B 17/3423* (2013.01); *A61B 17/3462* (2013.01); *A61B 1/3132* (2013.01); *A61B 17/29* (2013.01); *A61B 2017/347* (2013.01); *A61B 2017/349* (2013.01); *A61B 2017/3445* (2013.01)

(58) Field of Classification Search
USPC ........................................................ 600/137
See application file for complete search history.

(56) References Cited

U.S. PATENT DOCUMENTS

| | | | |
|---|---|---|---|
| 5,713,869 A * | 2/1998 | Morejon | A61B 17/3421 604/164.01 |
| 6,007,519 A * | 12/1999 | Rosselli | A61M 25/0606 604/164.01 |
| 6,086,530 A * | 7/2000 | Mack | A61B 1/00135 600/121 |
| 8,066,630 B2 | 11/2011 | Oberlaender et al. | |
| 2009/0177039 A1* | 7/2009 | Frank | A61B 17/29 600/137 |
| 2015/0080650 A1 | 3/2015 | Dejima | |
| 2016/0235279 A1 | 8/2016 | Yamakawa | |

FOREIGN PATENT DOCUMENTS

| | | |
|---|---|---|
| WO | 2013/176167 | 11/2013 |
| WO | 2015/033906 | 3/2015 |

OTHER PUBLICATIONS

"Search Report of Europe Counterpart Application", dated Febraury 17, 2017, p. 1-p. 6, in which the listed references were cited.

\* cited by examiner

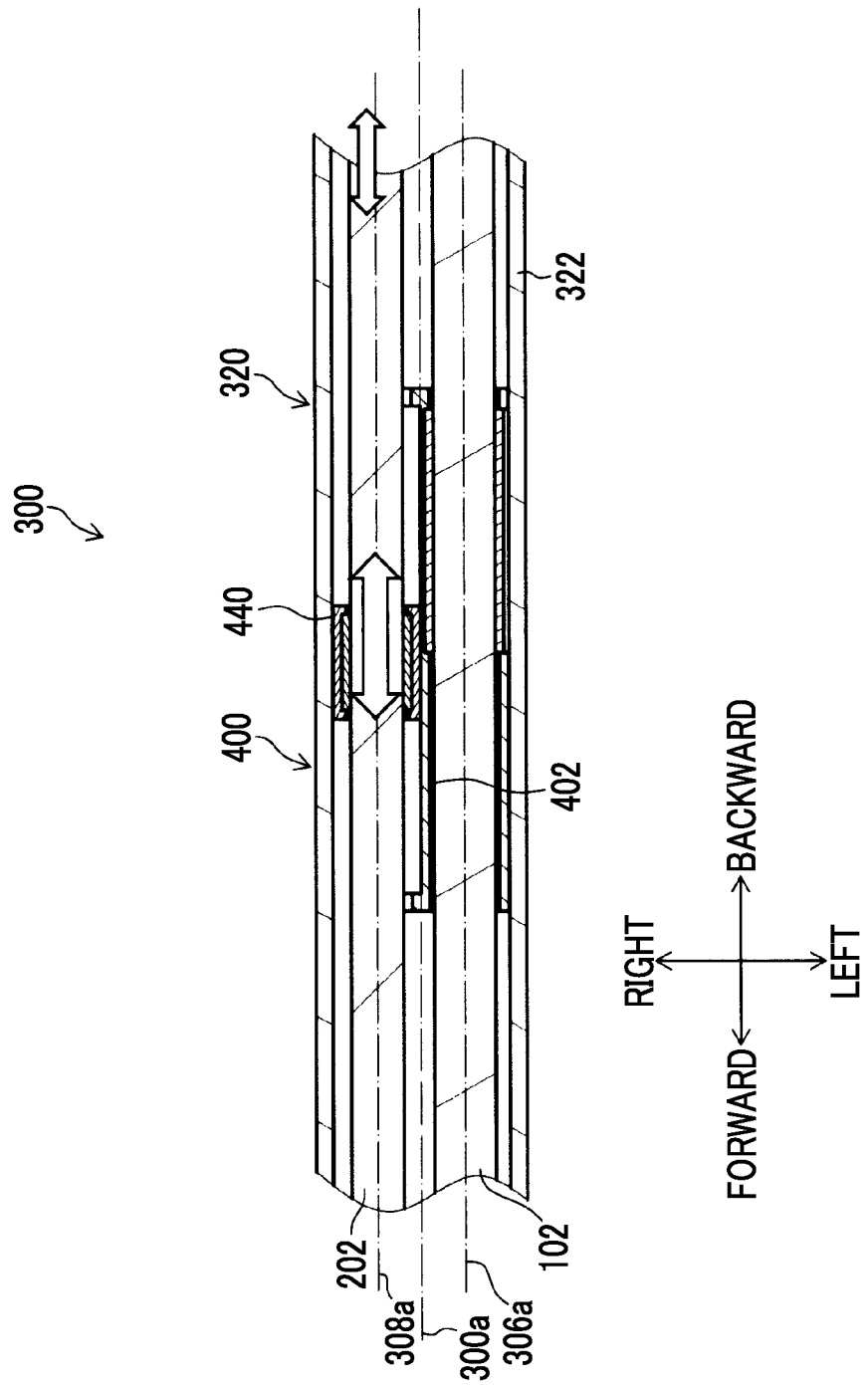

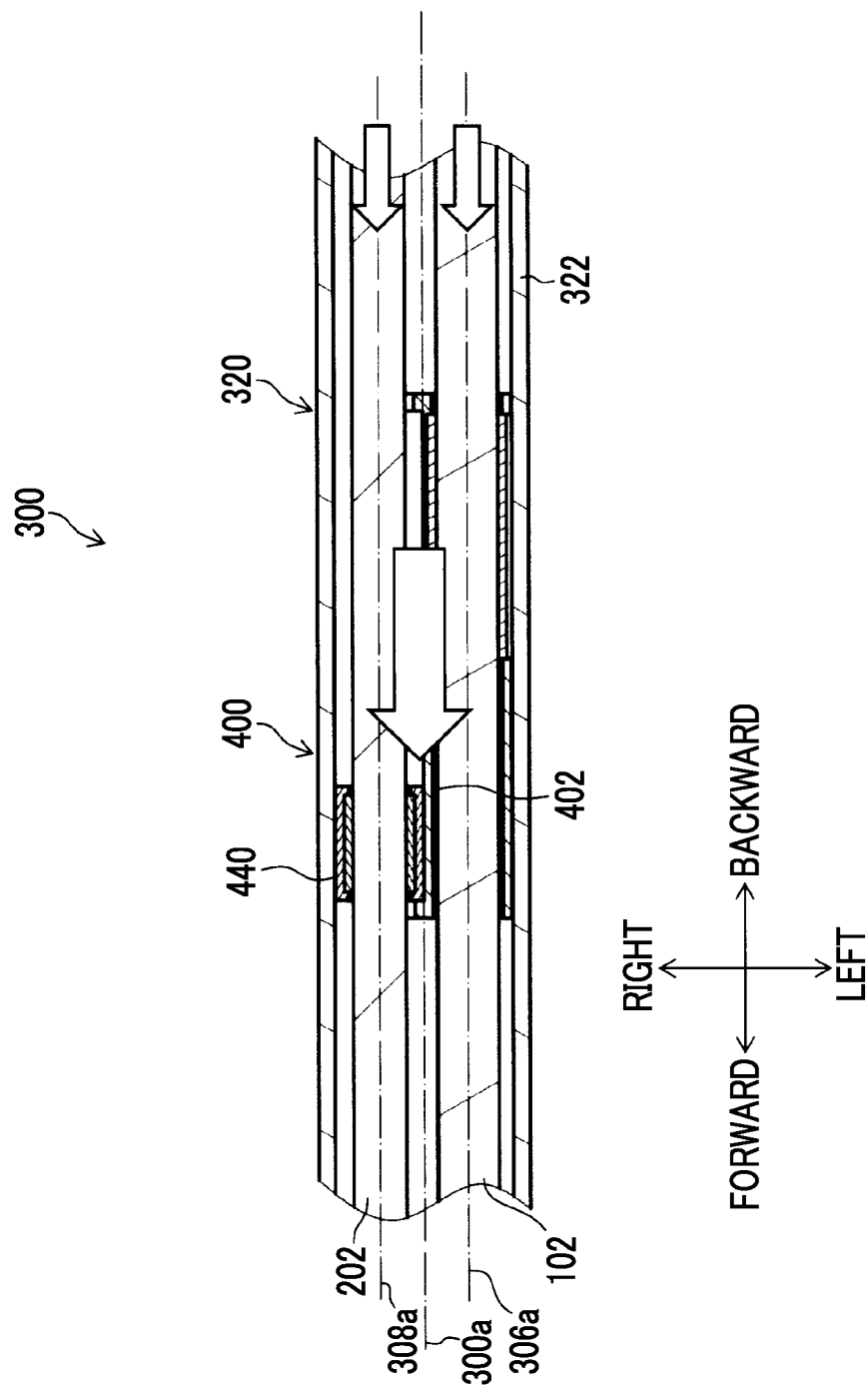

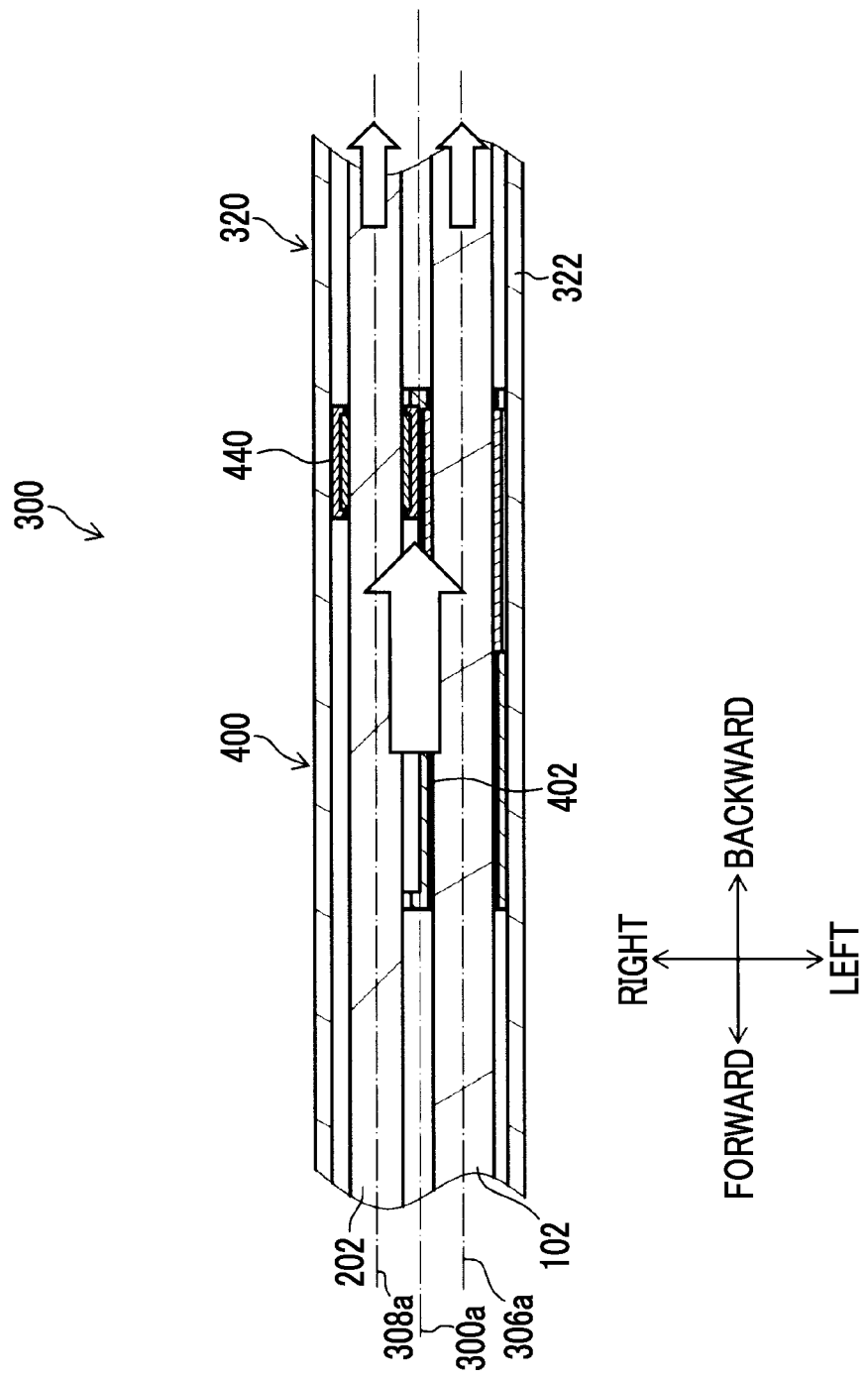

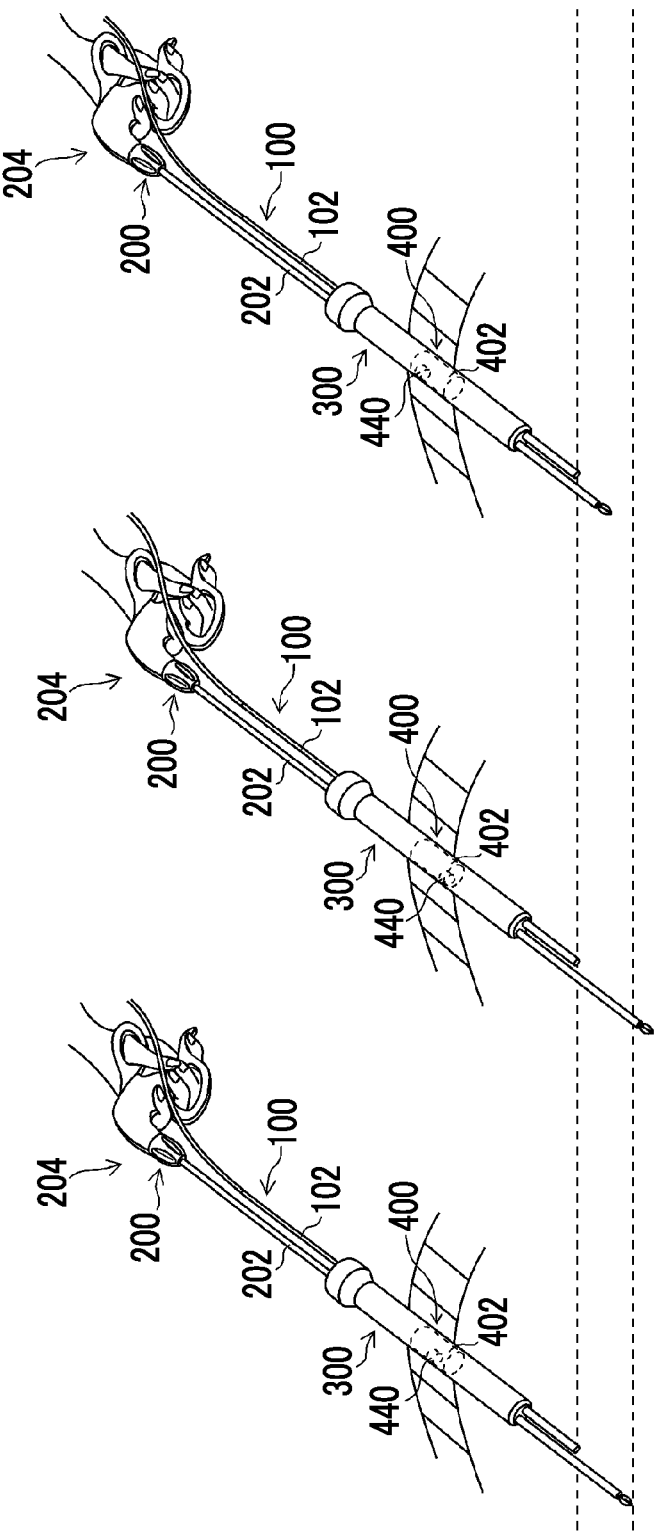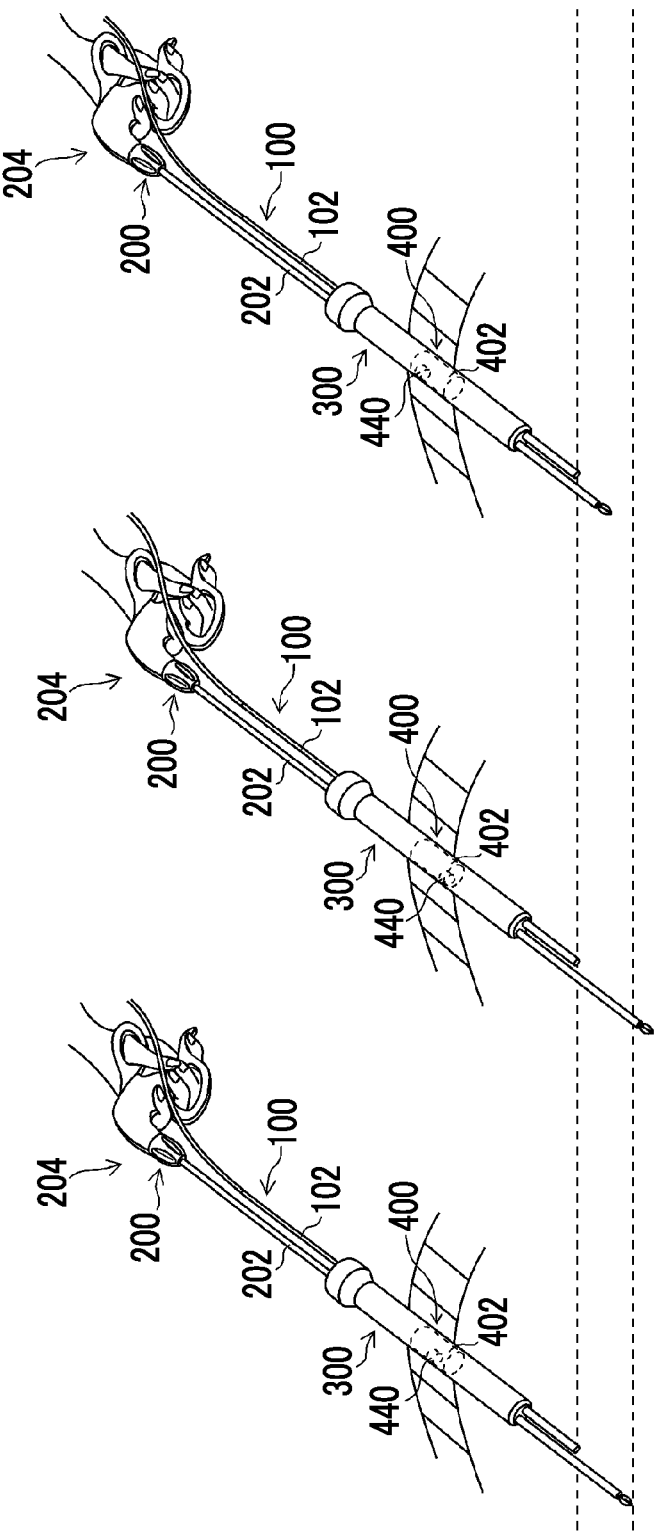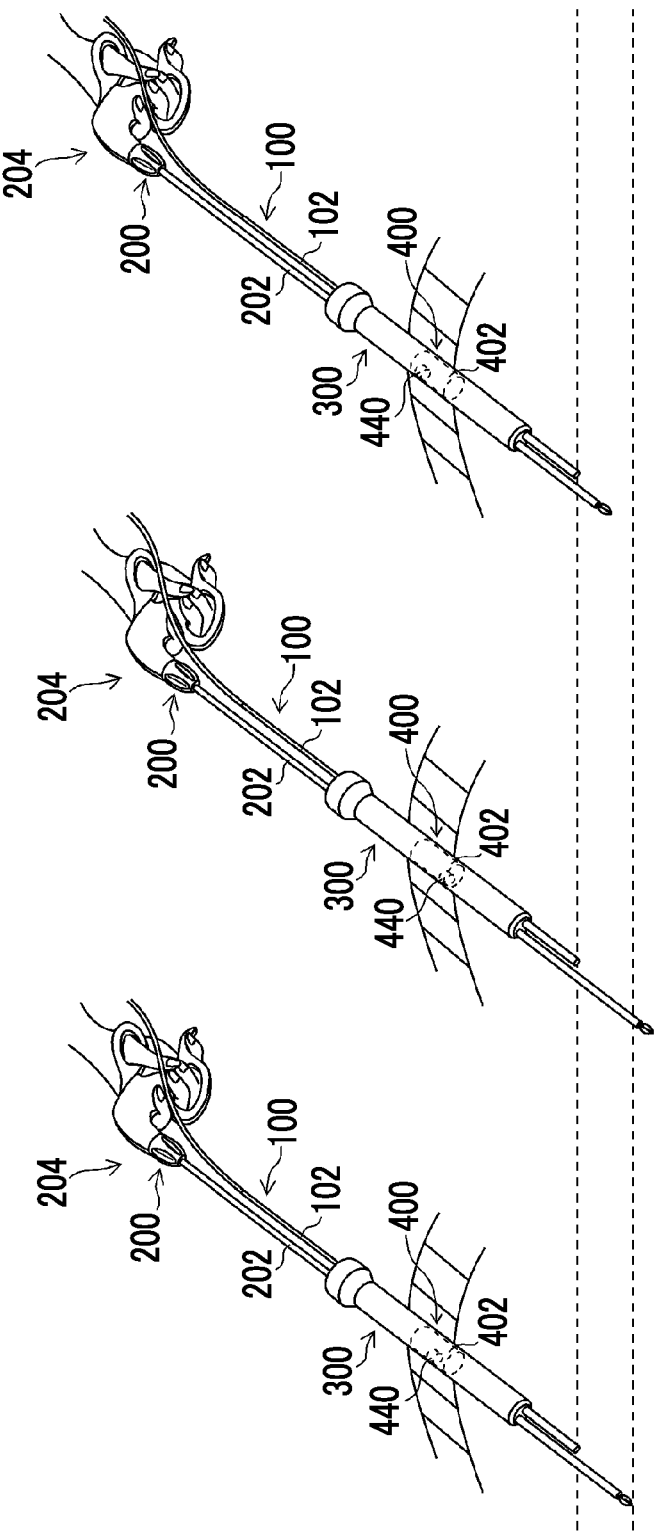

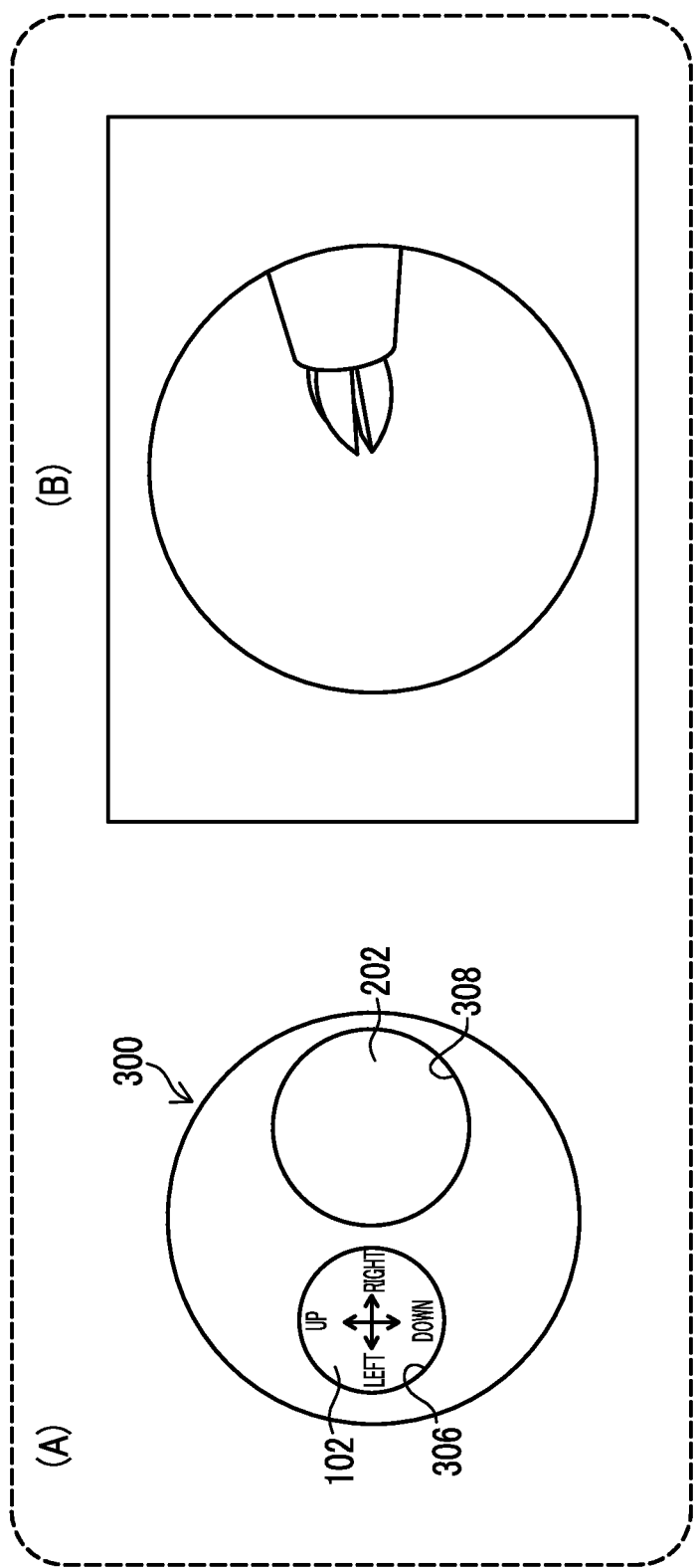

SHEATHING TUBE AND ENDOSCOPIC SURGICAL DEVICE

CROSS-REFERENCE TO RELATED APPLICATIONS

This application is a Continuation of PCT International Application No. PCT/JP2015/059355 filed on Mar, 26, 2015, which claims priority under 35 U.S.C. § 119(a) to U.S. Provisional Application No. 61/971,272 filed on Mar. 27, 2014. Each of the above applications is hereby expressly incorporated by reference, in their entirety, into the present application.

BACKGROUND OF THE INVENTION

1. Field of the Invention

The present invention relates to a sheathing tube and an endoscopic surgical device, and particularly, to a sheathing tube sheathing a tubular member, such as an overtube used in endoscopic surgery, and an endoscopic surgical device.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, has been widely performed. In endoscopic surgery, a plurality of holes are made in a patient's body wall, an endoscope is inserted into a body cavity from one hole of these, and a treatment tool is inserted into the body cavity from another hole. Then, treatment of a living body tissue is performed with the treatment tool while observing the living body tissue within the body cavity with the endoscope.

Generally, in endoscopic surgery, one or a plurality of treatment tools are used simultaneously with the endoscope. Therefore, since it is difficult for one surgeon to simultaneously operate the endoscope and the plurality of treatment tools, for example, a task, such as operating a treatment tool that the surgeon holds with his/her hands while making an assistant called an endoscopic technician operate the endoscope is normally performed.

In this way, in endoscopic surgery, it is usual that the surgeon's hands are occupied by the operation of the treatment tool, and the operation of the endoscope is performed by the assistant. Therefore, in a case where the observation position of the endoscope is changed, the surgeon needs to give sequential instructions to the assistant. Hence, the task of correctly directing the orientation of the endoscope to a direction desired by the surgeon is difficult, and stress is likely to be imposed on the surgeon. Additionally, since the assistant performs an operation after the surgeon issues an instruction, there is a tendency that surgery time is likely to be prolonged. Additionally, the assistant needs to operate the endoscope so as not to interfere with a surgeon's procedure, and the operation is likely to become complicated.

In contrast, the present applicant suggests a technique in which an endoscope and a treatment tool are combined together using an overtube, and if the treatment tool is moved forward and backward, the endoscope is also moved forward and backward in an interlocking manner with this movement of the treatment tool (refer to WO2013/176167A). Specifically, the overtube that guides an insertion part of the endoscope and an insertion part of the treatment tool into a body cavity includes a cylindrical overtube body that is inserted in a state where the insertion part of the endoscope and the insertion part of the treatment tool are made to be parallel to each other, a movable body that is movable in an axial direction and has an endoscope holding part and a treatment tool holding part is provided inside the overtube body, the insertion part of the endoscope and the insertion part of the treatment tool are held by the respective holding parts in a state where the insertion parts are made to be parallel to each other, and if the insertion part of the treatment tool is moved in the axial direction, the insertion part of the endoscope also moves in the axial direction in an interlocking manner with this movement. Accordingly, the number of holes made in the patient's body wall can be reduced, the invasion to the patient can be reduced, and the visual field of the endoscope can be easily changed while a surgeon operates the treatment tool without asking for an assistant's help.

SUMMARY OF THE INVENTION

However, in the technique that the present applicant has suggested earlier, if the overtube rotates around the axis, the insertion part of the endoscope and the insertion part of the treatment tool may co-rotate with the rotation of the overtube, and a visible state of the treatment tool with respect to a diseased site may differ in an observation image (endoscope image) obtained by the endoscope. Therefore, the overtube needs to be fixed to the body wall so as not to rotate around the axis.

Meanwhile, there may be a desire to change a positional relationship between the insertion part of the endoscope and the insertion part of the treatment tool depending on the details of treatment, or the like. In this case, in order to change the positional relationship between the insertion part of the endoscope and the insertion part of the treatment tool, it is necessary to rotate the overtube around the axis with respect to a body wall. However, if the overtube is fixed so as not to rotate around the axis, complicated operation and a lot of operating force are required in order to release the fixation.

The invention has been made in view of such circumstances, and an object thereof is to provide a sheathing tube and an endoscopic surgical device capable of selectively switching between a state where a tubular member (overtube or the like) is rotatable around an axial direction and a state where the tubular member is not rotatable, with a simple operation.

In order to achieve the above object, a sheathing tube related to an aspect of the invention is a sheathing tube sheathing a tubular member. The sheathing tube includes a first cylindrical member having a distal end opening from which the tubular member is delivered; a second cylindrical member that is rotatably connected to a base end of the first cylindrical member and has a base end opening into which the tubular member is introduced; rotation restriction means (rotation restriction part) that is provided in the second cylindrical member and restricts rotation of the tubular member with respect to the second cylindrical member; a spring member that is arranged between the first cylindrical member and the second cylindrical member and is deformable between a rotation locked state where rotation of the second cylindrical member with respect to the first cylindrical member is restricted by engagement of the spring member with the base end of the first cylindrical member, and a rotation unlocked state where the engagement is released and the rotation of the second cylindrical member with respect to the first cylindrical member is allowed; and a rotation operating member that is rotatably provided in an axial direction of the second cylindrical member and deforms the spring member between the rotation locked state and the rotation unlocked state.

According to this aspect, the sheathing tube sheathing the tubular member has the first cylindrical member and the second cylindrical member, and is able to switch between the rotation locked state where the rotation of the second cylindrical member with respect to the first cylindrical member is restricted by the engagement of the spring member arranged between the first cylindrical member and second cylindrical member, and the rotation unlocked state where the engagement using the spring member is released and the rotation of the second cylindrical member with respect to the first cylindrical member is allowed, according to the rotational operation of the rotation operating member. Therefore, it is possible to selectively switch between a state where the tubular member is rotatable around the axis and a state where the tubular member is not rotatable, with a simple operation.

For this reason, in a case where the rotation operating member is not rotationally operated, the rotation locked state where the rotation of the second cylindrical member with respect to the first cylindrical member is restricted by the engagement using the spring member can be brought about, and in a case where the rotation operating member is rotationally operated, the rotation unlocked state where the engagement using the spring member is released can be brought about. Therefore, an operator can rotate the tubular member easily without being conscious of the operation of releasing the engagement using the spring member.

In the sheathing tube related to the aspect of the invention, an aspect in which an internal diameter of a distal end of the second cylindrical member is larger than an external diameter of the base end of the first cylindrical member, and the distal end of the second cylindrical member is arranged so as to cover the base end of the first cylindrical member, and the spring member is arranged between the distal end of the second cylindrical member and the base end of the first cylindrical member is preferable.

In the sheathing tube related to the aspect of the invention, an aspect in which the spring member includes a C-shaped spring member having a cutout part formed in a portion thereof in a circumferential direction, the spring member includes a projection part protruding toward outside in a radial direction, and the projection part is engaged with an engaging groove provided inside the second cylindrical member, and thereby, rotation of the spring member with respect to the second cylindrical member is restricted, and the rotation operating member includes a locking part locked to the cutout part, and in a case where the rotation operating member is rotationally operated, the spring member is deformed from the rotation locked state to the rotation unlocked state by expanding an opening width of the cutout part in a state where the locking part is locked to the cutout part is preferable.

In the sheathing tube related to the aspect of the invention, an aspect in which the tubular member is an overtube that guides an insertion part of a medical instrument to be inserted into a body cavity into the body cavity is preferable.

An endoscopic surgical device related to another aspect of the invention is an endoscopic surgical device including an overtube that guides an insertion part of a medical instrument to be inserted into a body cavity into the body cavity; and a sheathing tube sheathing the overtube. The sheathing tube includes a first cylindrical member having a distal end opening from which the overtube is delivered, a second cylindrical member that is rotatably connected to a base end of the first cylindrical member and has a base end opening into which the overtube is introduced, rotation restriction means that is provided in the second cylindrical member and restricts rotation of the overtube with respect to the second cylindrical member, a spring member that is disposed between the first cylindrical member and the second cylindrical member and is deformable between a rotation locked state where rotation of the second cylindrical member with respect to the first cylindrical member is restricted by engagement of the spring member with the base end of the first cylindrical member, and a rotation unlocked state where the engagement is released and the rotation of the second cylindrical member with respect to the first cylindrical member is allowed, and a rotation operating member that is rotatably provided in an axial direction of the second cylindrical member and deforms the spring member between the rotation locked state and the rotation unlocked state.

According to the invention, it is possible to selectively switch between a state where the tubular member is rotatable around the axis and a state where the tubular member is not rotatable, with a simple operation.

BRIEF DESCRIPTION OF THE DRAWINGS

FIG. 7 is an explanatory view used for the description of the action of the slider.

FIG. 8 is an explanatory view used for the description of the action of the slider.

FIG. 9 is an explanatory view used for the description of the action of the slider.

FIGS. 10A to 10C are explanatory views illustrating an aspect of the operation when treatment of a diseased site within a patient's body cavity is performed using the endoscopic surgical device.

FIG. 13A is a view illustrating a positional relationship between the endoscope insertion part and a treatment tool insertion part inserted through the overtube, and an observation image.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
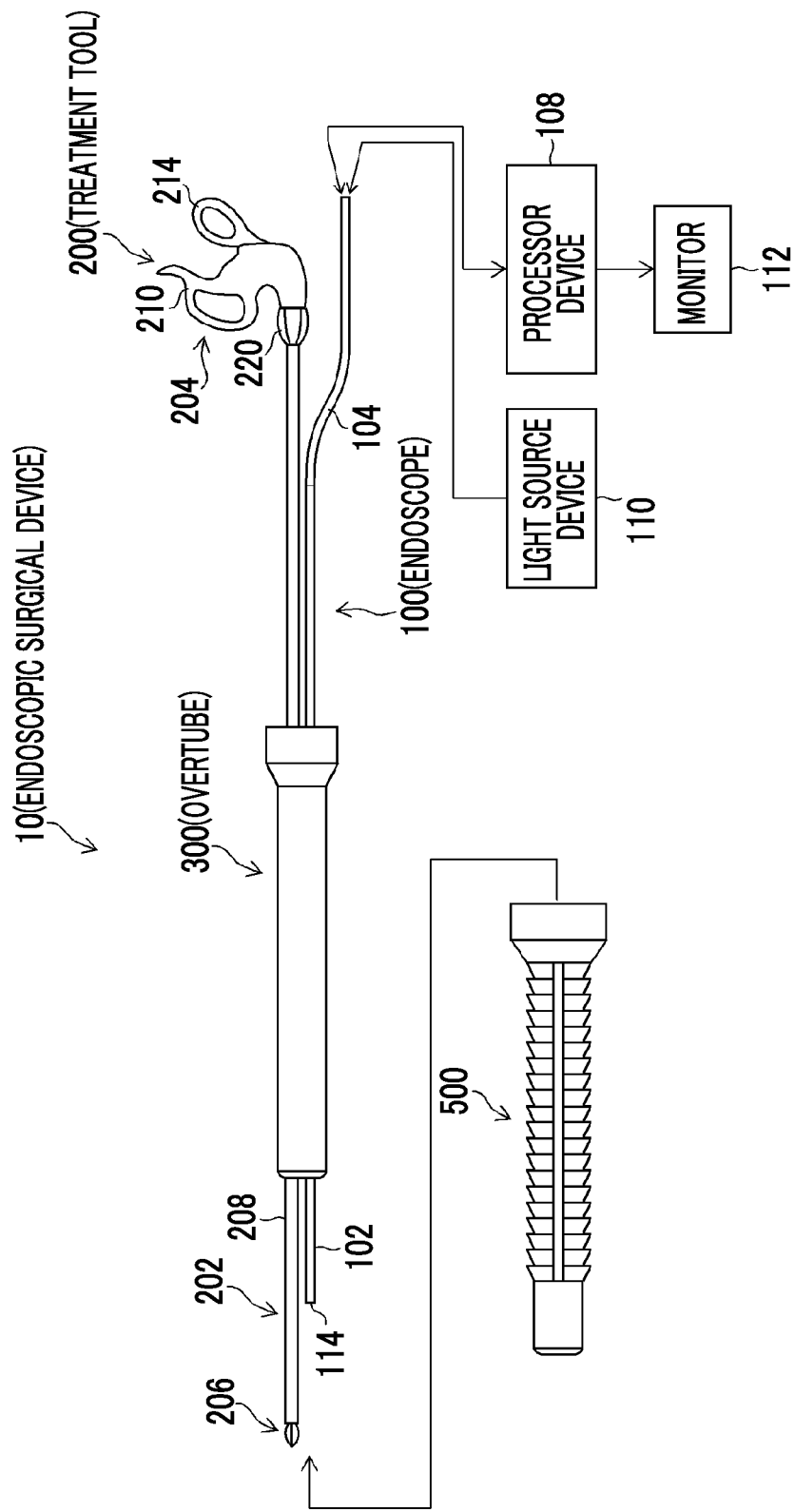
FIG. 1 is a schematic block diagram of an endoscopic surgical device related to the invention.

FIG. 1 is a schematic block diagram of an endoscopic surgical device related to the invention. As illustrated in FIG. 1, an endoscopic surgical device 10 includes an endoscope 100 that observes the inside of a patient's body cavity, a treatment tool 200 for examining or treating a diseased site within the patient's body cavity, an overtube 300 that is inserted into a body wall and guides the endoscope 100 and the treatment tool 200 into the body cavity, and an outer port 500 (sheathing tube) fitted to the overtube 300.

The endoscope 100 is, for example, a hard endoscope, such as a laparoscope, and includes an insertion part 102 (hereinafter referred to as "endoscope insertion part") that is inserted into a body cavity and has an outer peripheral part surrounded by an elongated hard cylindrical body, and a cable part 104 that is provided continuously with a base end side of the endoscope insertion part 102 and that has an outer peripheral part surrounded by an elongated flexible cylindrical body.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
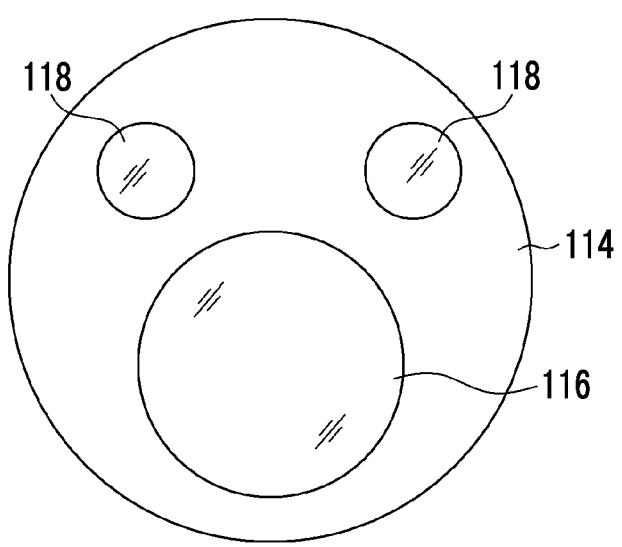
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and an image pick-up element, such as a charge coupled device (CCD) or a complementary metal oxide semiconductor (CMOS), which is arranged at an image pick-up position of the objective lens, are disposed behind the observation window 116. A signal cable (not illustrated) connected to this image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

As illustrated in FIG. 1, the treatment tool 200 consists of, for example, forceps, and includes an elongated insertion part 202 (hereinafter referred to as a "treatment tool insertion part") that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a cylindrical sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end of the operating shaft is coupled to the movable handle 214.

The treatment part 206 is provided with a pair of gripping members that is openable and closable. The gripping members are coupled to a distal end of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the overtube 300 allows the endoscope insertion part 102 and the treatment tool insertion part 202, which are inserted thereinto from the base end side, to be inserted therethrough and delivered from the distal end side. By inserting the overtube 300 into a body wall and having a distal end side thereof arranged outside of the body and a base end side thereof arranged within the body cavity, it is possible to guide the endoscope insertion part 102 and the treatment tool insertion part 202 into the body cavity with one overtube 300. Additionally, the overtube 300 includes an interlocking function of interlocking the endoscope insertion part 102 with the treatment tool insertion part 202 to move these insertion parts forward and backward as will be described below in detail. For example, the endoscope insertion part 102 can also be moved forward and backward by the forward and backward movement operation of only the treatment tool insertion part 202, and a suitable observation image can be obtained without performing the forward and backward movement operation of the endoscope insertion part 102.

Figure 3:
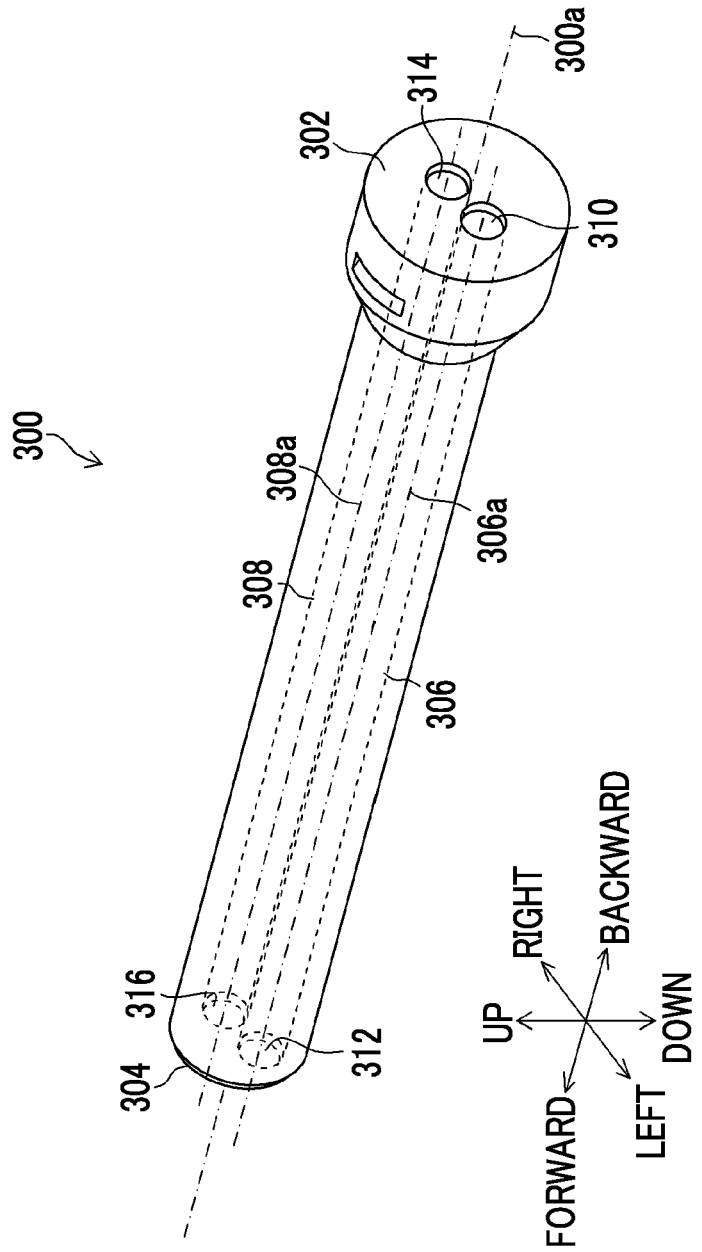
FIG. 3 is an external perspective view illustrating an overtube.

FIG. 3 is an external perspective view illustrating the overtube 300.

As illustrated in this drawing, the overtube 300 has an elongated columnar shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a (longitudinal axis) indicating a central axis of the overtube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axes of the endoscope insertion part 102 and the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are arranged on the same plane. However, a configuration in which the reference axis 300a, the endoscope insertion axis 306a, and the treatment tool insertion axis 308a are arranged on the same plane may not be adopted.

In addition, regarding the position and orientation of a space where the overtube 300 has been arranged, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the overtube 300 is provided with an endoscope insertion port 310 that is a base end opening that allows the endoscope insertion part 102 to be inserted into the endoscope insertion passage 306 therethrough, and a treatment tool insertion port 314 that is base end opening that allows the treatment tool insertion part 202 to be inserted into the treatment tool insertion passage 308 therethrough.

The distal end surface 304 of the overtube 300 is provided with an endoscope delivery port 312 that is a distal end opening that allows the endoscope insertion part 102 inserted into the endoscope insertion passage 306 to be delivered to the outside therethrough, and a treatment tool delivery port 316 that is a distal end opening that allows the treatment tool insertion part 202 inserted into the treatment tool insertion passage 308 to be delivered to the outside therethrough.

Figure 4:
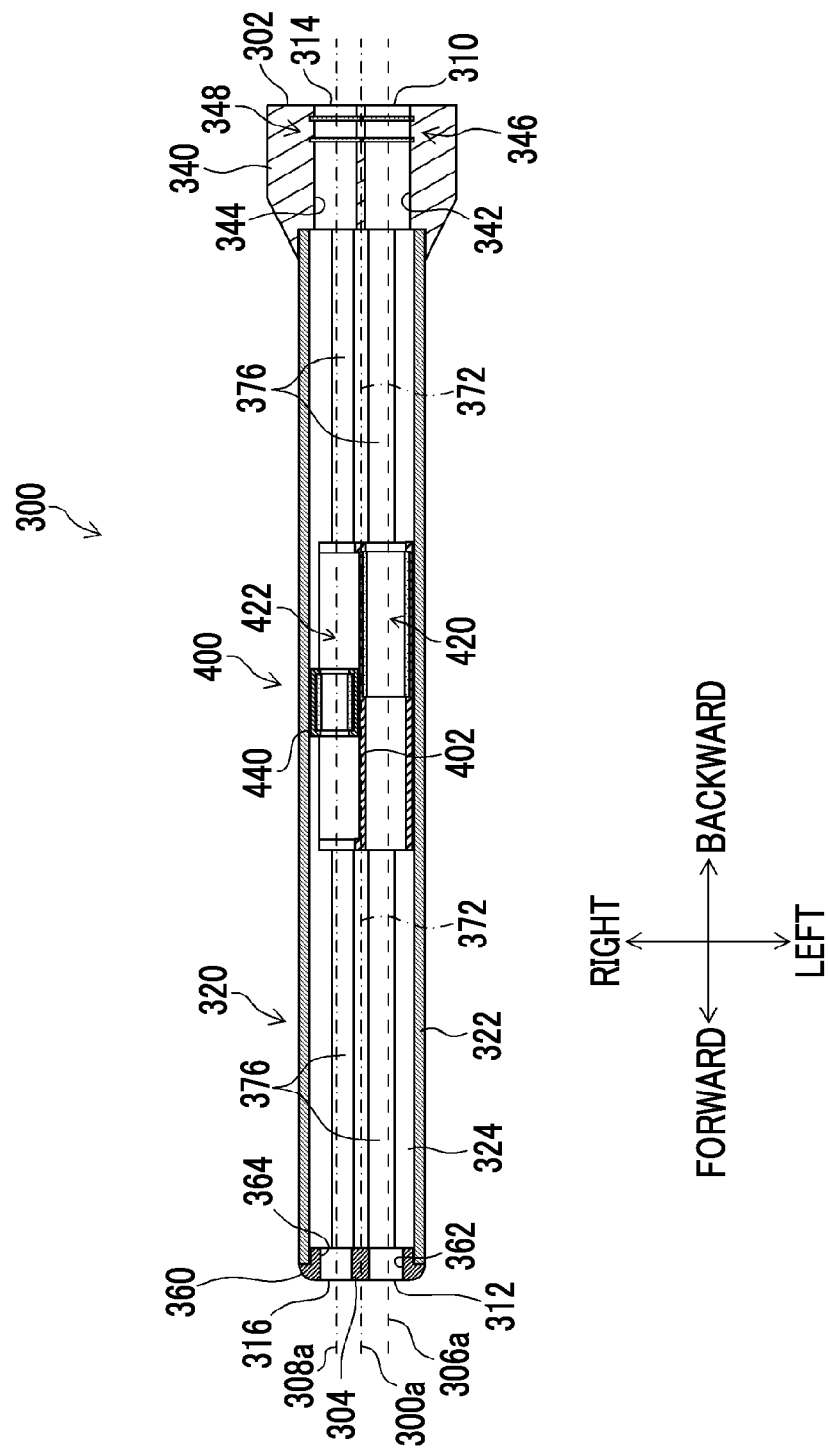
FIG. 4 is a sectional view illustrating the internal structure of the overtube.

FIG. 4 is a sectional view illustrating the internal structure of the overtube 300, and illustrates a section cut in a plane that includes the reference axis 300a and is orthogonal to an upward-downward direction (cut in a leftward-rightward direction along the reference axis 300a).

As illustrated in this drawing, the overtube 300 has an overtube body 320 that occupies substantially the entire area in the forward-backward direction, a base end cap 340 that is attached to a rear end (base end) of the overtube 300, a distal end cap 360 that is attached to a distal end, and a slider 400 (an interlocking member) that is arranged inside the overtube 300.

The overtube body 320 is formed in an elongated cylindrical shape having the reference axis 300a as a central axis using hard resins, metals, or the like, and has an outer wall 322 that surrounds an outer periphery, and a cavity part 324 that penetrates from a base end of the overtube body 320 to a distal end thereof.

The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the overtube body 320 using hard resins, metals, or the like, and a rear end surface thereof constitutes the base end surface 302 of the overtube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described endoscope insertion port 310, and an opening of the through-hole 344 is equivalent to the above-described treatment tool insertion port 314.

Additionally, the through-holes 342 and 344 are provided with valve members 346 and 348. The valve members 346 and 348, for example, open in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a front end surface thereof constitutes the distal end surface 304 of the overtube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described endoscope delivery port 312, and an opening of the through-hole 364 is equivalent to the treatment tool delivery port 316.

The above base end cap 340 and the above distal end cap 360 are some of the constituent elements of the overtube body of the invention, and may be formed separately from or formed integrally with the overtube body 320.

The slider 400 is housed within (the cavity part 324) the overtube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of either the endoscope insertion part 102 or the treatment tool insertion part 202 in the forward-backward direction (axial direction) does not interlock with the movement of the other and a sensing zone where the forward and backward movement of either the endoscope insertion part 102 or the treatment tool insertion part 202 interlocks with the movement of the other. That is, the endoscope insertion part 102 is adapted to interlock with the forward and backward movement of the treatment tool insertion part 202 in the axial direction with play by the slider 400.

Figure 5:
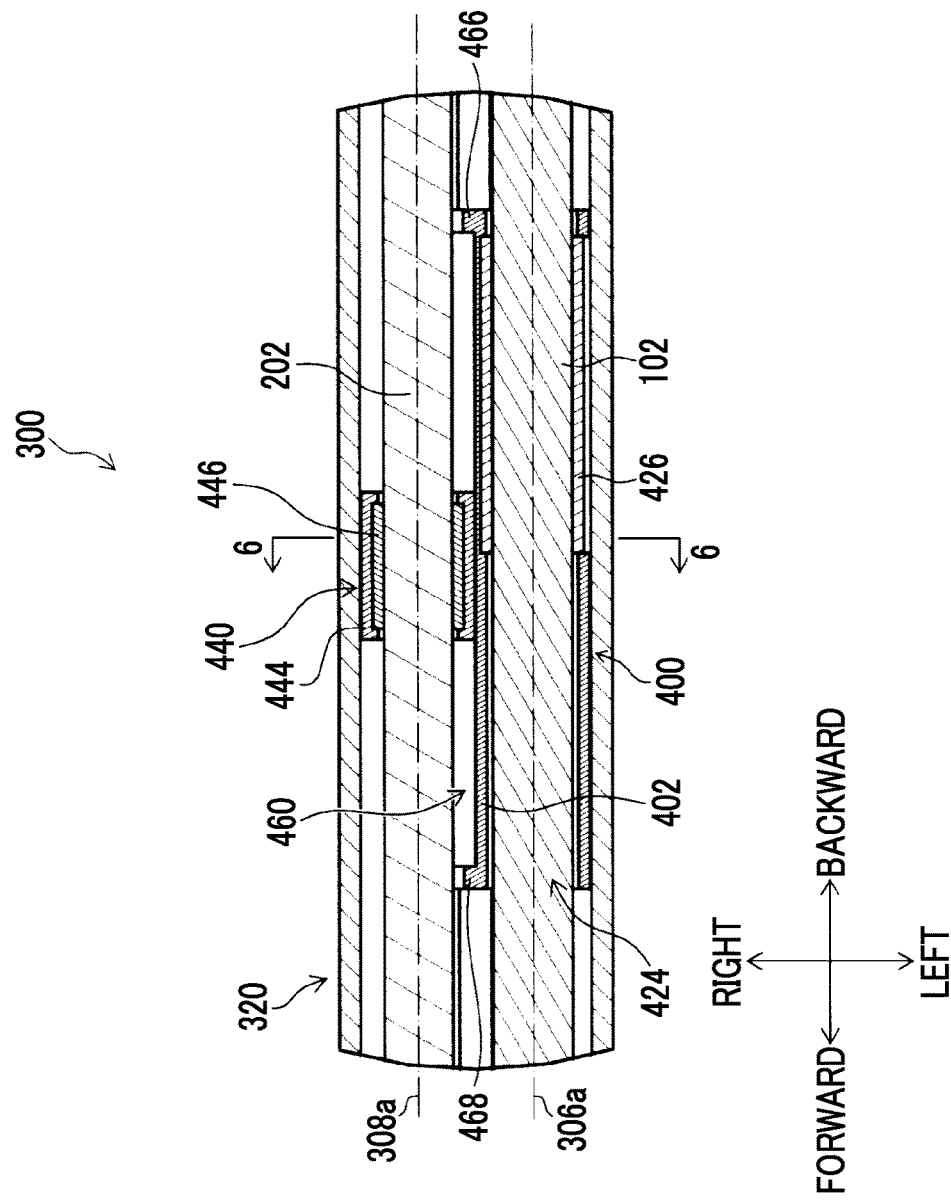
FIG. 5 is an enlarged sectional view illustrating a portion of FIG. 4 in an enlarged manner.
Figure 6:
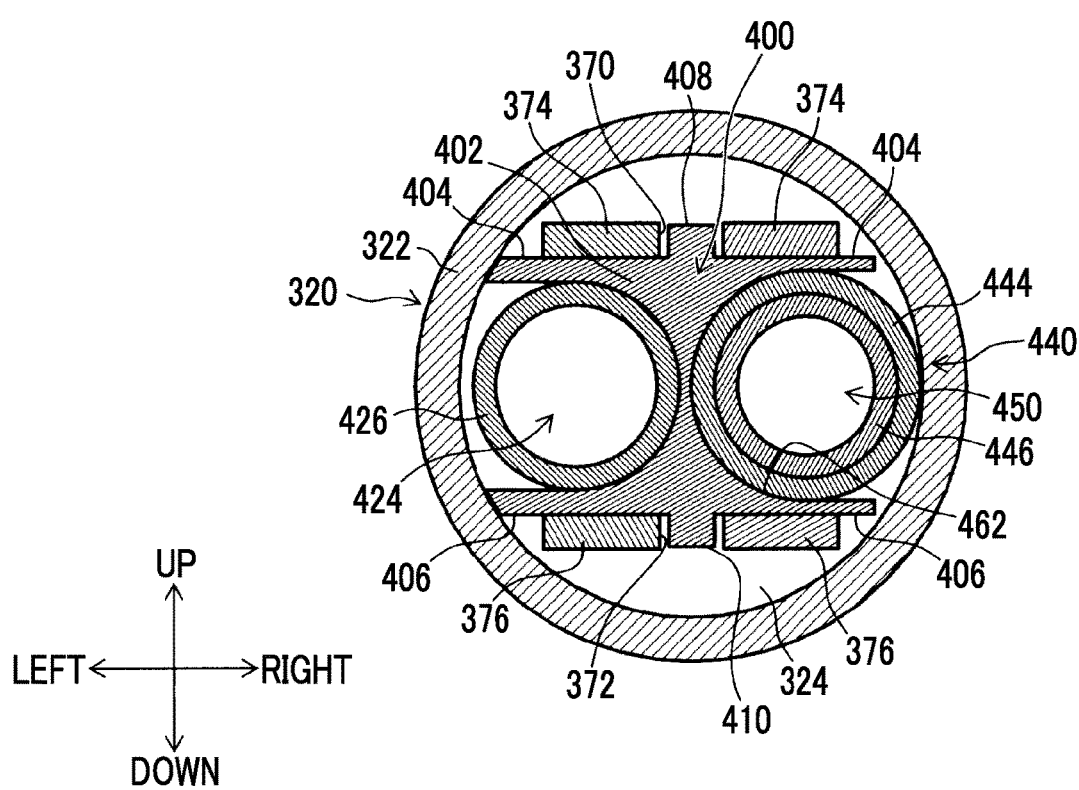
FIG. 6 is a sectional view when viewed from arrow 6-6 in FIG. 5.

FIG. 5 is an enlarged sectional view illustrating a portion, in which the slider 400 is arranged in FIG. 4, in an enlarged manner, and illustrates a state where the endoscope insertion part 102 and the treatment tool insertion part 202 have been inserted through the endoscope insertion passage 306 and the treatment tool insertion passage 308, respectively. FIG. 6 is a sectional view when viewed from arrow 6-6 in FIG. 5.

As illustrated in FIGS. 5 and 6, the slider 400 has a slider body 402 (slider member) that holds components of the slider 400. As illustrated in FIG. 6, protruding strips 408 and 410 that extend in the direction (forward-backward direction) of the reference axis 300a are formed on a flat upper surface 404 and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360, are respectively supported by an upper part and a lower part within the overtube body 320, and guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the overtube body 320, and the upper surface 404 and the lower surface 406 are arranged in a state where these surfaces have contacted or approached the guide plates 374 and 374 and the guide plates 376 and 376.

Accordingly, the slider 400 is supported so as to be movable forward and backward in the forward-backward direction within the overtube body 320, and is supported in a state where the movement of the slider in the upward-downward direction and in the leftward-rightward direction and the rotation of the slider in all directions (direction around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 arranged within the overtube body 320, and may be formed in the outer wall 322 of the overtube body 320 or may be formed by other configurations.

Additionally, the slider 400, as illustrated in FIG. 4, has an endoscope-coupled part 420 that is coupled to (engaged with) the endoscope insertion part 102, and a treatment tool-coupled part 422 that is coupled to (engaged with) the treatment tool insertion part 202.

The endoscope-coupled part 420 is provided on the left side of the slider body 402, and includes a through-hole 424 (refer to FIG. 6) in which a space serving as the endoscope insertion passage 306 is secured within the overtube body 320 and through which, as illustrated in FIG. 5, the endoscope insertion part 102 is inserted, and a pressure-contact member 426 that is fixed to the through-hole 424, is brought into pressure contact with the outer peripheral surface (side surface) of the endoscope insertion part 102 inserted through the endoscope insertion passage 306. The pressure-contact member 426 is annularly formed of elastic materials, such as elastic rubber, as illustrated in FIG. 6.

Accordingly, when the endoscope insertion part 102 has been inserted through the endoscope insertion passage 306, as illustrated in FIG. 5, the endoscope insertion part 102 is inserted through the through-hole 424, the pressure-contact member 426 is brought into pressure contact with (engaged with) the outer peripheral surface of the endoscope insertion part 102, and the central axis of the endoscope insertion part 102 is arranged coaxially with the endoscope insertion axis 306a.

The endoscope insertion part 102 and the slider 400 (slider body 402) are coupled to (engaged with) each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupled part 422, as illustrated in FIG. 4, is provided on the right side of the slider body 402, and as illustrated in FIG. 5, includes a sleeve 440 (sleeve member) that is coupled to the treatment tool insertion part 202, and a guide part 460 that guides the sleeve 440 so as to be movable forward and backward in the forward-backward direction.

The sleeve 440, as illustrated in FIG. 6, includes a sleeve body (frame body) 444 formed in a cylindrical shape, and a pressure-contact member 446 fixed to the inside of the sleeve body 444. The pressure-contact member 446 is annularly formed of elastic materials, such as elastic rubber.

Accordingly, when the treatment tool insertion part 202 has been inserted through the treatment tool insertion passage 308, as illustrated in FIG. 5, the treatment tool insertion part 202 is inserted through the inside (the through-hole 450 of FIG. 6) of the pressure-contact member 446, the pressure-contact member 446 is brought into pressure contact with (engaged with) the outer peripheral surface of the treatment tool insertion part 202, and the central axis of the treatment tool insertion part 202 is arranged coaxially with the treatment tool insertion axis 308a.

The treatment tool insertion part 202 and the sleeve 440 are coupled with each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupled part 422, as illustrated in FIG. 6, is formed by a space surrounded by a guide surface 462 of the slider body 402 that extends in the direction of the reference axis 300a within the cavity part 324 of the overtube body 320, and an inner peripheral surface of the overtube body 320. The sleeve 440 is housed and arranged in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIG. 5, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 arranged in the space of the guide part 460 moves forward and backward in the forward-backward direction.

Therefore, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

According to the slider 400 configured as described above, the endoscope insertion part 102 inserted through the endoscope insertion passage 306 of the overtube 300 and the slider body 402 are coupled together, and the treatment tool insertion part 202 inserted through the treatment tool insertion passage 308 of the overtube 300 and the sleeve 440 are coupled together.

As illustrated in FIG. 7, it is supposed that a surgeon performs a forward and backward movement operation for moving the treatment tool insertion part 202 forward and backward in the axial direction (forward-backward direction) in a state where the sleeve 440 has not reached the rear end and the front end of the movable range thereof with respect to the slider body 402 (guide part 460).

In this case, in a case where the sleeve 440 has moved forward and backward within the movable range thereof with respect to the slider body 402, the slider body 402 does not move with respect to the forward and backward movement of the treatment tool insertion part 202. Therefore, a forward and backward movement operation in the dead zone where the endoscope insertion part 102 does not interlock with the forward and backward movement of the treatment tool insertion part 202 is performed.

Meanwhile, as illustrated in FIG. 8, if the treatment tool insertion part 202 is operated to move forward in a state where the sleeve 440 reaches the front end of the movable range thereof with respect to the slider body 402, the sleeve 440 and the slider body 402 move forward with respect to the overtube body 320 together with the treatment tool insertion part 202. Accordingly, a forward and backward movement operation in the sensing zone where the endoscope insertion part 102 moves forward in an interlocking manner with the treatment tool insertion part 202 is performed.

Similarly, as illustrated in FIG. 9, if the treatment tool insertion part 202 is operated to move backward in a state where the sleeve 440 reaches the rear end of the movable range thereof with respect to the slider body 402, the sleeve 440 and the slider body 402 move backward with respect to the overtube body 320 together with the treatment tool insertion part 202. Accordingly, a forward and backward movement operation in the sensing zone where the endoscope insertion part 102 moves backward in an interlocking manner with the treatment tool insertion part 202 is performed.

Therefore, in a case where the treatment tool insertion part 202 has been greatly displaced in the axial direction as described above (in a case where a large amplitude of forward and backward movement has been performed), the endoscope insertion part 102 is displaced in the axial direction in an interlocking manner with the treatment tool insertion part 202, and in a case where the displacement of the treatment tool insertion part 202 in the axial direction is small (in a case where a small amplitude of forward and backward movement is performed), the endoscope insertion part 102 is not displaced in the axial direction.

Accordingly, in a case where the displacement of the treatment tool insertion part 202 in the axial direction is large (in a case where a large amplitude of forward and backward movement has been performed) when a surgeon has moved the treatment tool insertion part 202 forward and backward in the axial direction, the endoscope insertion part 102 also moves in an interlocking manner forward, backward, up, down, right, and left. Thus, the visual field, orientation, and the like of the endoscope 100 can be changed as intended by a surgeon. Additionally, the visual field is always given to pick up an image of the distal end of the treatment tool and consequently, an image that is optimal for treatment is automatically provided. In a case where it is desired to check sites other than a site to be treated, the checking can be performed by moving the treatment tool insertion part 202, and a surgeon can perform operations as desired. Therefore, an assistant (endoscopic technician) who operates the endoscope 100 apart from the surgeon can be made unnecessary, and a troublesome condition in which the surgeon should instruct an assistant about the visual field, orientation, and the like of the endoscope serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, the size of an object to be observed within an observation image can be prevented from fluctuating unnecessarily, a sense of perspective can be suitably maintained, and a stable observation image can be provided.

Figure 11A:
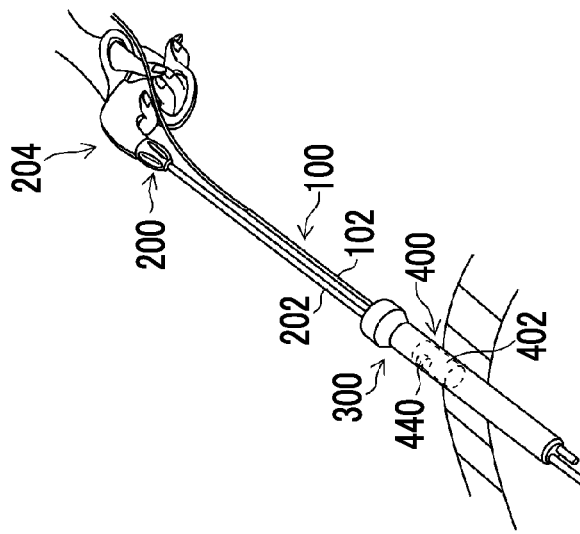
FIGS. 11A to 11C are explanatory views illustrating an aspect of the operation when the treatment of the diseased site within the patient's body cavity is performed using the endoscopic surgical device.
Figure 11B:
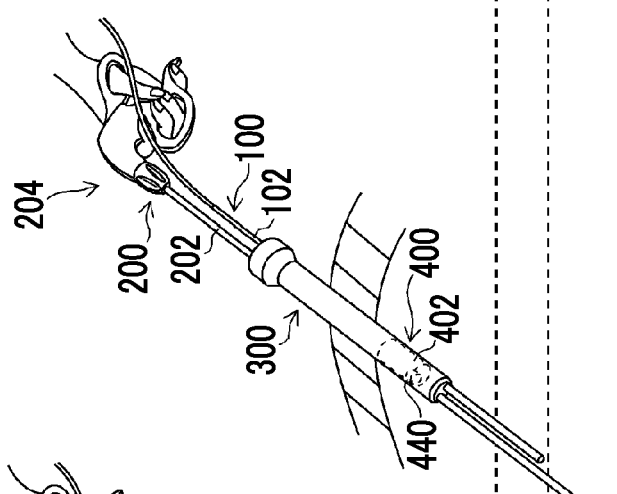
Figure 11C:
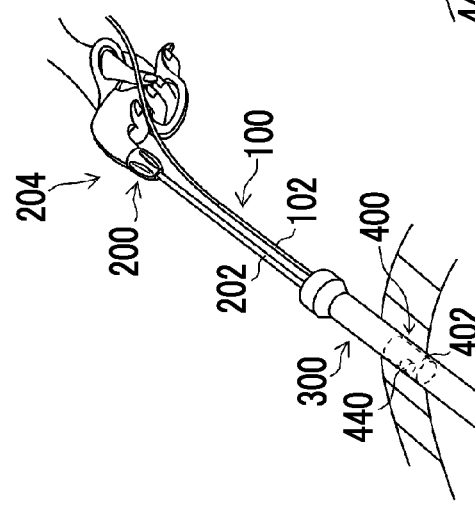

FIGS. 10A to 11C are explanatory views illustrating aspects of the operation when treatment of a diseased site within a patient's body cavity is performed using the endoscopic surgical device 10 of the present embodiment, FIGS. 10A to 10C illustrate an aspect of the operation (the forward and backward movement operation in the dead zone) when only the treatment tool 200 moves forward and backward, and FIGS. 11A to 11C illustrate an aspect of the operation (forward and backward movement operation in the sensing zone) when the treatment tool 200 moves forward and backward in an interlocking manner with the endoscope 100.

As illustrated in FIG. 10A, the endoscope 100 (endoscope insertion part 102) and the treatment tool 200 (treatment tool insertion part 202) are respectively inserted into the endoscope insertion passage 306 and the treatment tool insertion passage 308 of the overtube 300 after the overtube 300 is inserted into a patient's body wall and a pneumoperitoneum gas is injected into a body cavity. In this case, the endoscope 100 is coupled to the slider body 402 of the slider 400, and the treatment tool 200 is coupled to the sleeve 440 of the slider 400. Thus, when the sleeve 440 moves within a movable range thereof with respect to the slider body 402, the interlocking is performed with the dead zone (play) where the endoscope 100 does not interlock with the forward and backward movement of the treatment tool 200.

In this state, if the surgeon grips the operating part 204 of the treatment tool 200 and minutely moves the treatment tool 200 forward, only the treatment tool 200 moves forward in a state where the endoscope 100 is stationary as illustrated in FIG. 10B, with respect to the forward movement in the dead zone until the sleeve 440 of the slider 400 abuts against the front end of the movable range thereof.

Similarly, if the surgeon grips the operating part 204 of the treatment tool 200 and minutely moves the treatment tool 200 backward, only the treatment tool 200 moves backward in a state where the endoscope 100 is stationary as illustrated in FIG. 10C, with respect to the backward movement in the dead zone until the sleeve 440 of the slider 400 abuts against the rear end of the movable range thereof.

Therefore, since the endoscope 100 does not move forward and backward with respect to the minute forward and backward movement operation of the treatment tool 200, that is, the forward and backward movement operation thereof in the dead zone, the range of an observation image displayed on the monitor 112 does not change, the size of an object to be observed can be prevented from fluctuating in response to the minute displacement of the treatment tool 200, a sense of perspective can be suitably maintained, and a stable observation image can be obtained.

FIG. 11A illustrates that the overtube 300, the endoscope 100, and the treatment tool 200 are in the same state as those of FIG. 10A.

In this state, if the surgeon grips the operating part 204 of the treatment tool 200 and greatly moves the treatment tool 200 forward, the endoscope 100 moves forward in an interlocking manner with the forward movement of the treatment tool 200 through an interlocking function of the slider 400 as illustrated in FIG. 11B, after the forward movement in the dead zone until the sleeve 440 of the slider 400 abuts against the front end of the movable range.

Similarly, if the surgeon grips the operating part 204 of the treatment tool 200 and greatly moves the treatment tool 200 backward, the endoscope 100 moves backward in an interlocking manner with the backward movement of the treatment tool 200 through the interlocking function of the slider 400 as illustrated in FIG. 11C, after the backward movement in the dead zone until the sleeve 440 of the slider 400 abuts against the rear end of the movable range.

Therefore, since the endoscope 100 moves forward and backward with respect to a large forward and backward movement operation of the treatment tool 200, that is, the forward and backward movement operation thereof in the sensing zone, the range of an observation image displayed on the monitor 112 is continuously changed so as to follow the forward and backward movement of the treatment tool 200. Accordingly, since the size of an object to be observed changes in response to the operation of the treatment tool 200, an image desired by a surgeon can be simply obtained.

Next, the sheathing tube 500 (outer port) illustrated in FIG. 1 will be described.

Special machining is not performed on an outer peripheral surface of the above-described overtube 300 (overtube body 320), and when the operation of the treatment tool 200, or the like is performed by inserting the endoscope insertion part 102 and the treatment tool insertion part 202 through the overtube after being inserted into a body wall, there is a possibility that the overtube 300 may rotate around (around the axis) the reference axis 300a unintentionally with respect to the body wall or may move forward and backward in the direction (axial direction) of the reference axis 300a.

Particularly, the overtube 300 has a problem in that the position of the distal end of the endoscope insertion part 102 may fluctuate and an observation visual field may fluctuate if the overtube 300 rotates around the axis unlike an overtube through which only the endoscope insertion part 102 is inserted.

Figure 12:
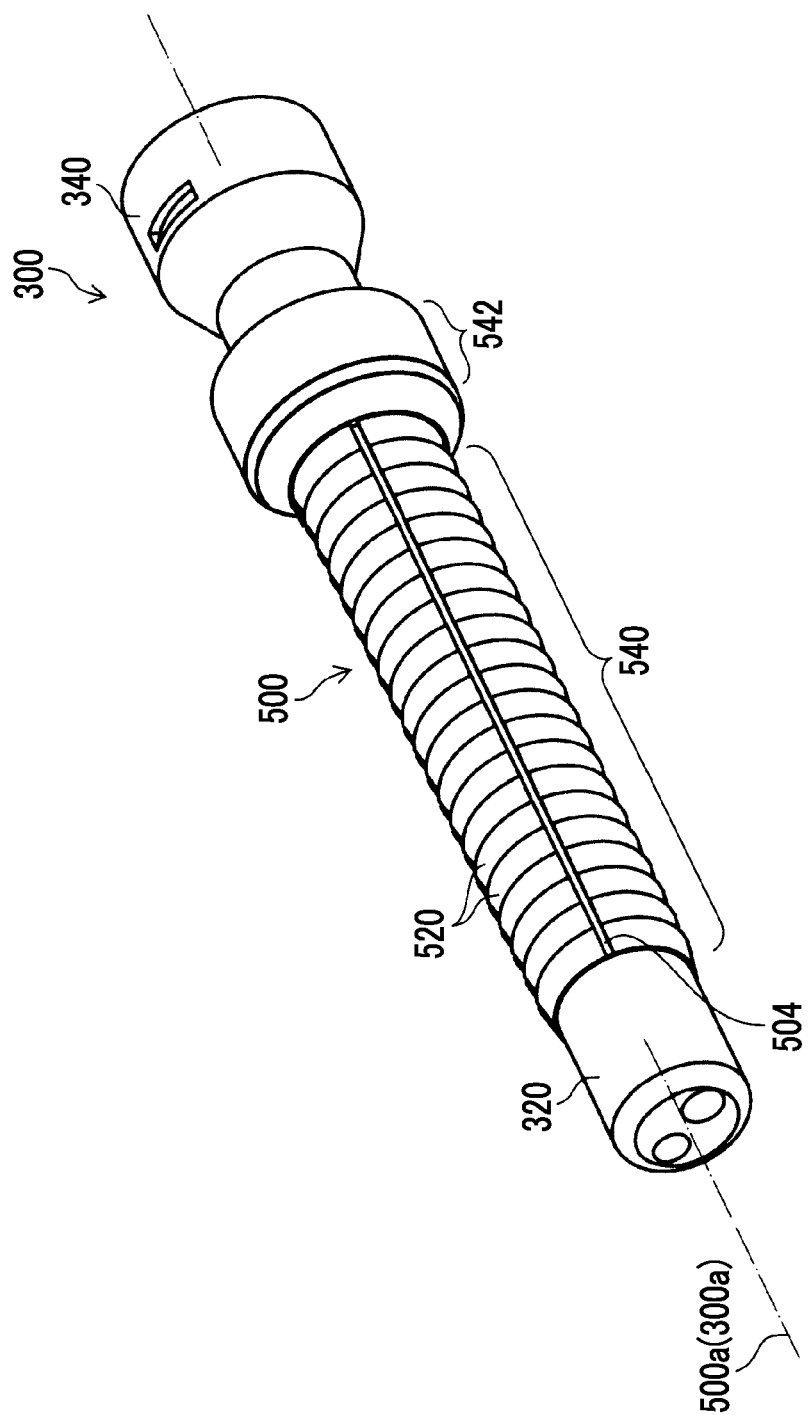
FIG. 12 is a perspective view illustrating a state where an outer port is fitted to the overtube.

Thus, by fitting (sheathing) and fixing the outer port 500, having a wall surface that prevents the rotation of the overtube around the axis with respect to a body wall and the forward and backward movement of the overtube in the axial direction, to the outer peripheral surface of the overtube 300 as illustrated in FIG. 12, unintended rotation and forward and backward movement of the overtube 300 with respect to the body wall can be prevented.

Meanwhile, a situation in which the rotational angle of the overtube 300 around the axis with respect to the body wall is to be changed may occur after the overtube 300 to which the outer port 500 is fitted is inserted into the body wall.

Figure 13B:
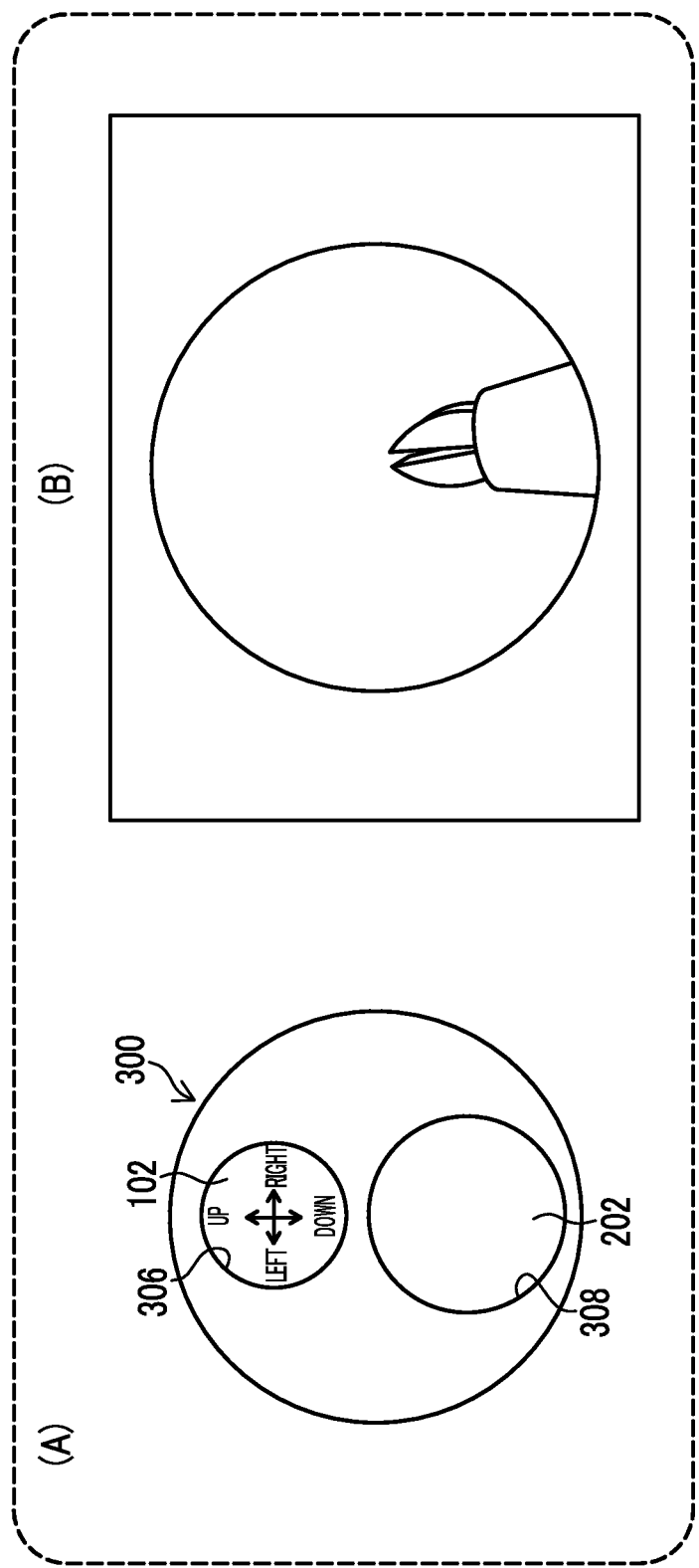
FIG. 13B is a view illustrating a positional relationship between the endoscope insertion part and the treatment tool insertion part inserted through the overtube, and an observation image.

For example, in cases where a positional relationship between the endoscope insertion part 102 and the treatment tool insertion part 202 that are respectively inserted through the endoscope insertion passage 306 and the treatment tool insertion passage 308 of the overtube 300 inserted into a body wall is left and right like part (B) of FIG. 13A and is up and down like part (A) of FIG. 13B, a positional relationship between the treatment part 206 of the treatment tool 200 and a treatment target on an observation image obtained by the endoscope 100 is different like part (A) of FIG. 13A and part (B) of FIG. 13B. Therefore, a situation in which the rotational angle of the overtube 300 around the axis with respect to the body wall is to be changed so that treatment is easily performed in response to situations occurs.

In addition, FIGS. 13A and 13B illustrates a case where the vertical and horizontal directions of the endoscope 100 are maintained so as to become the same when the endoscope insertion part 102 rotates relative to the overtube 300.

Thus, the outer port 500 of the present embodiment is adapted to be able to release the fixed state (rotation locked state) of rotation thereof around the axis with respect to the overtube 300, and is adapted to be able to rotating the overtube 300 with respect to the outer port 500, thereby easily changing the rotational angle of the overtube 300 around the axis with respect to the body wall. That is, unlocking of the rotation of the overtube 300 and the rotation of the overtube are performed only through an operator's rotational operation, and the rotation of the overtube 300 is locked together with the end of the rotational operation. Accordingly, since it is not necessary to perform the operation of locking/unlocking of the overtube 300 separately from the rotational operation of the overtube, the rotational angle of the overtube 300 can be easily changed.

Figure 14:
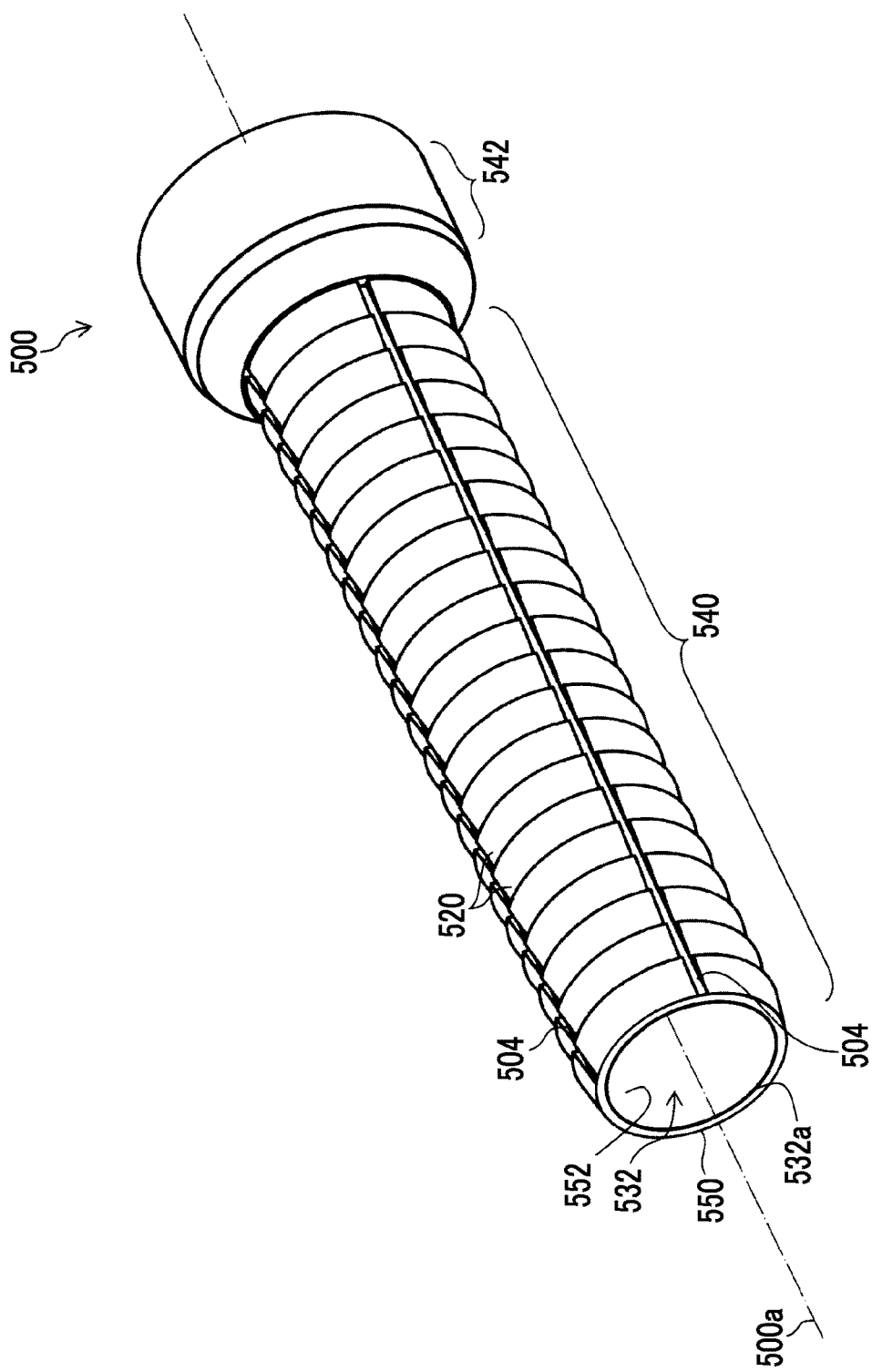
FIG. 14 is a perspective view of a sheathing tube.

FIG. 14 is a perspective view illustrating only the outer port 500.

As illustrated in FIGS. 12 and 14, the outer port 500 is formed in a long cylindrical shape having the reference axis 500a as a central axis, and has an insertion hole 532 that penetrates in the direction (axial direction) of the reference axis 500a from a base end of the outer port 500 to a distal end thereof.

The insertion hole 532 has a diameter of such a size that the overtube body 320 is movable forward and backward in the axial direction and is inserted therethrough so as to be rotatable in the direction around the axis.

If the overtube body 320 is inserted into the insertion hole 532 from the base end side and is moved forward, the overtube body 320 is delivered from the distal end side of the insertion hole 532. As illustrated in FIG. 12, the outer port 500 is fitted to the outer peripheral surface of the overtube body 320, and a desired position of the overtube body 320 is fixed to the outer port 500 by pressure contact of a pressure-contact member to be described below.

In addition, the axial length of the outer port 500 is shorter than the axial length (the length of a portion closer to the distal end side than a front end of the base end cap 340 of the overtube 300) of the overtube body 320, and the outer port 500 falls within the axial range of the overtube body 320.

The outer port 500 is constituted of a sheathing tube insertion part 540 (first cylindrical member) on the distal end side, and a base end 542 connected to the base end side from a base end of the sheathing tube insertion part 540.

The sheathing tube insertion part 540 is a portion that is inserted into a body wall together with the overtube body 320 inserted through the insertion hole 532 and is insertable into holes (ports) of the body wall and a body cavity, and has a distal end opening 532a, from which the overtube body 320 inserted through the insertion hole 532 is delivered, on the distal end side.

The sheathing tube insertion part 540 has a long cylindrical outer wall 550 having the reference axis 500a as a central axis, a long cylindrical inner tube 552 extending in the direction of the reference axis 500a in a range from a distal end of the sheathing tube insertion part 540 to the base end 542 is arranged inside the outer wall 550, and the outer wall 550 is fixed in a state where the outer wall is brought into close contact with an outer peripheral surface of the inner tube 552.

A cavity inside the inner tube 552 constitutes a portion of the above-described insertion hole 532 through which the overtube body 320 is inserted, and has substantially the same diameter as the external diameter of the overtube body 320.

Therefore, as illustrated in FIG. 12, an inner peripheral surface of the inner tube 552 of the outer port 500 contacts or approaches the outer peripheral surface of the overtube body 320 without a substantial gap, in a state where the overtube body 320 is inserted through the insertion hole 532 of the outer port 500, and the outer wall 550 of the sheathing tube insertion part 540 of the outer port 500 is arranged at a proximity position along the outer peripheral surface of the overtube body 320. Additionally, the reference axis 500a of the outer port 500 in this case is arranged substantially coaxially with the reference axis 300a of the overtube 300.

Irregularities that restrict unintended fluctuations with respect to a body wall are formed in an outer peripheral part of the outer wall 550. As one specific form of the irregularities of the outer peripheral part, four longitudinal grooves 504 that restrict rotation in the direction around the axis with respect to a body wall and a large number of lateral grooves 520 of that restrict forward and backward movement in the axial direction with respect to the body wall are formed.

Each longitudinal groove 504 is linearly formed in the direction of the reference axis 500a, and four longitudinal grooves 504 are formed at 90-degree intervals in the direction (a rotational direction centered on the reference axis 500a) around the axis.

According to the longitudinal grooves 504, since cells of a body wall enters each longitudinal groove 504 when the overtube 300 to which the outer port 500 is fitted is inserted into the body wall, resistance is generated with respect to the rotation of the overtube 300 around the axis, and the unintended rotation of the overtube 300 around the axis is prevented.

In addition, although the number of longitudinal grooves 504 is four in the present form, the number of longitudinal grooves may be a number other than four.

Each lateral groove 520 is annularly formed in the direction around the axis, and a number of lateral grooves 520 are periodically formed in the direction of the reference axis 500a.

Figure 15:
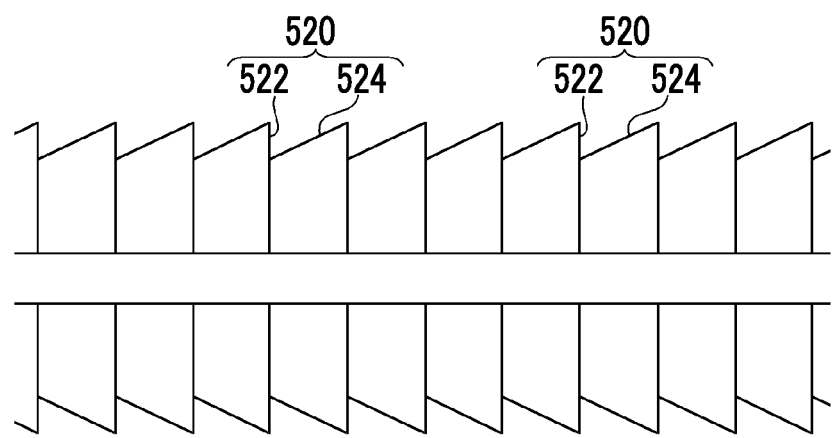
FIG. 15 is an enlarged view of an outer wall of the sheathing tube.

Each lateral groove 520 is formed from a side surface 522 on the distal end side and a tapered surface 524 on the base end side as illustrated in FIG. 15 in which a portion of the outer wall 550 is enlarged, and the side surface 522 restricts the movement of the outer port 500 (overtube 300) to the base end side in the axial direction with respect to a body wall, and the tapered surface 524 restricts the movement of the outer port 500 (overtube 300) to the distal end side in the axial direction with respect to the body wall.

The inclination angle (an inclination angle with respect to the radial direction perpendicular to the reference axis 500a) of the side surface 522 is made smaller than the inclination angle (an inclination angle with respect to the radial direction perpendicular to the reference axis 500a) of the tapered surface 524. For example, the side surface 522 is formed parallel to the radial direction perpendicular to the reference axis 500a. In other words, the normal direction of the side surface 522 is formed parallel to the reference axis 500a.

In addition, the inclination angle of the side surface 522 is not limited to this, for example, may be within a range of 0 degree or more and 30 degrees or less, preferably, 0 degree or more and 15 degrees or less on the distal end side or on the base end side.

Meanwhile, the inclination angle of the tapered surface 524 may be larger than the inclination angle of the side surface 522, for example, may be within a range of 45 degrees or more and less than 90 degrees, and preferably 60 degrees or more and less than 90 degrees on the base end side with respect to the radial direction perpendicular to the reference axis 500a.

According to the lateral grooves 520, since cells of a body wall enters each lateral groove 520 when the overtube 300 to which the outer port 500 is fitted is inserted into the body wall, resistance is generated with respect to the forward and backward movement of the overtube 300 in the axial direction, and the unintended forward and backward movement of the overtube 300 in the axial direction is prevented.

Figure 16:
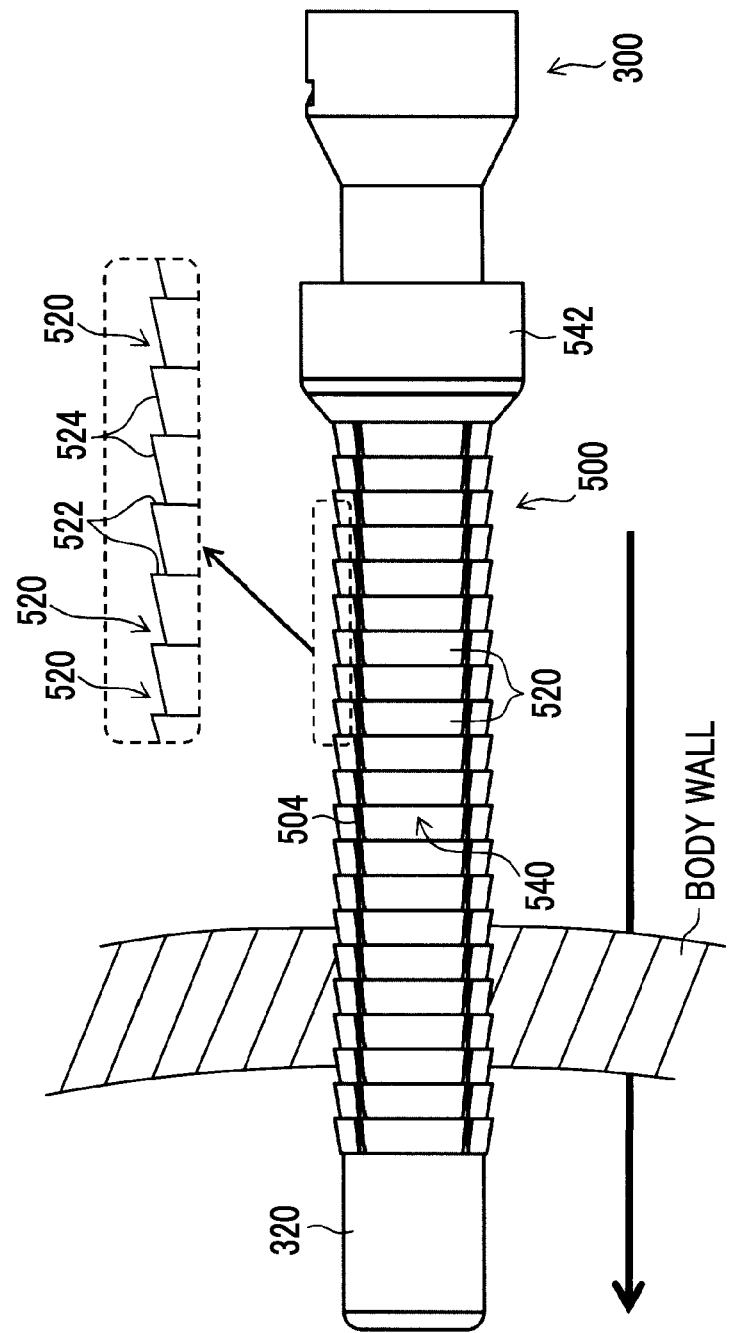
FIG. 16 is a view illustrating an aspect when an overtube to which the sheathing tube is fitted is inserted into a body wall.

Additionally, the movement of the overtube 300 is restricted by the tapered surface 524 of each lateral groove 520 when the overtube 300 is moved forward and backward (forward movement) to the distal end side in the axial direction with respect to a body wall, as illustrated in FIG. 16, as an aspect when the overtube 300 to which the outer port 500 is fitted is inserted into the body wall. In this case, as described above, the inclination angle of the tapered surface 524 is large. Thus, a large resistance force is not received as compared to a case where the overtube 300 is moved forward and backward (backward movement) to the base end side in the axial direction. Therefore, when the overtube 300 to which the outer port 500 is fitted is inserted into a body wall, the trouble that it becomes difficult to perform an insertion operation does not occur by virtue of the outer port 500, and the trouble that the lateral grooves 520 may crush the tissue of the body wall does not occur, either.

In addition, the form of the above-described irregularities formed in the outer peripheral part of the sheathing tube insertion part 540 (outer wall 550) of the outer port 500 may be an example, and may be other forms.

The base end 542 of the outer port 500 has a base end opening 532b (refer to a sectional view of FIG. 18), into which the overtube body 320 is introduced, on the base end side, and as illustrated in FIGS. 12 and 14, has a larger external diameter than the sheathing tube insertion part 540. Accordingly, the base end 542 is not inserted into holes of a body wall into which the sheathing tube insertion part 540 is inserted, and is arranged outside of the body. Therefore, even if the restriction of the forward movement of the overtube 300, to which the outer port 500 is fitted as described above, to a body wall, is weaker than the backward movement, the unintended movement of the overtube 300 to distal end side in the axial direction with respect to the body wall can also be reliably prevented by adjusting the position of the outer port 500 fixed to the overtube 300 (overtube body 320), thereby using the overtube at a position where the base end 542 is made to abut against the body wall.

Figure 17:
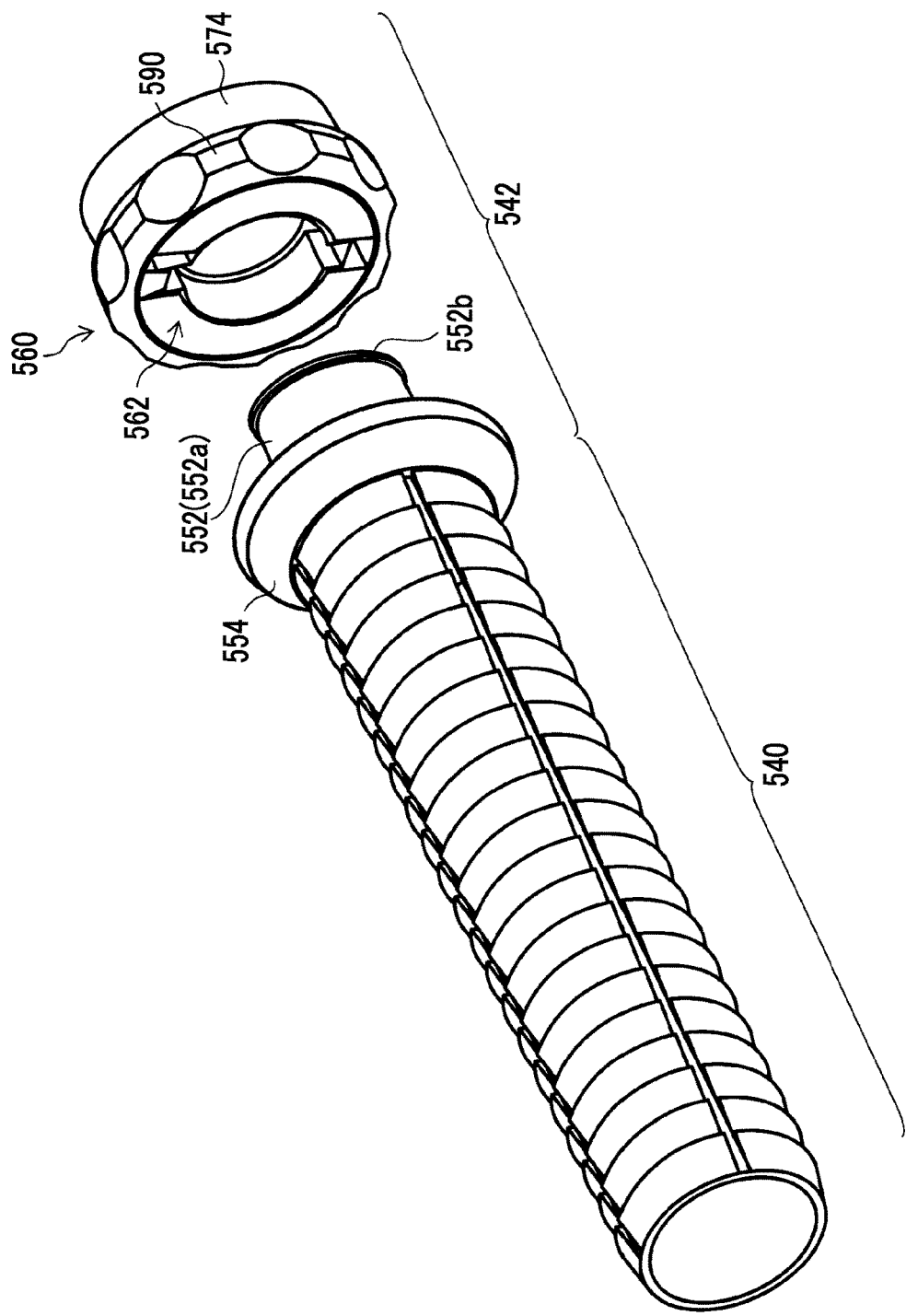
FIG. 17 is a partial exploded view of the sheathing tube.

Additionally, the base end 542, as illustrated in a partial exploded view of FIG. 17, consists of the inner tube 552 extending from the distal end of the sheathing tube insertion part 540 to the base end 542, an annular flange part 554 provided to protrude toward the outside from an outer peripheral surface of the inner tube 552, and a head part 560 (second cylindrical member).

The inner tube 552 extends further toward the base end side than the flange part 554, and if this portion is referred to as a head attachment part 552a (equivalent to a base end of the first cylindrical member), the head part 560 is mounted on the head attachment part 552a so as to abut against the surface of the flange part 554 on the base end side.

Figure 18:
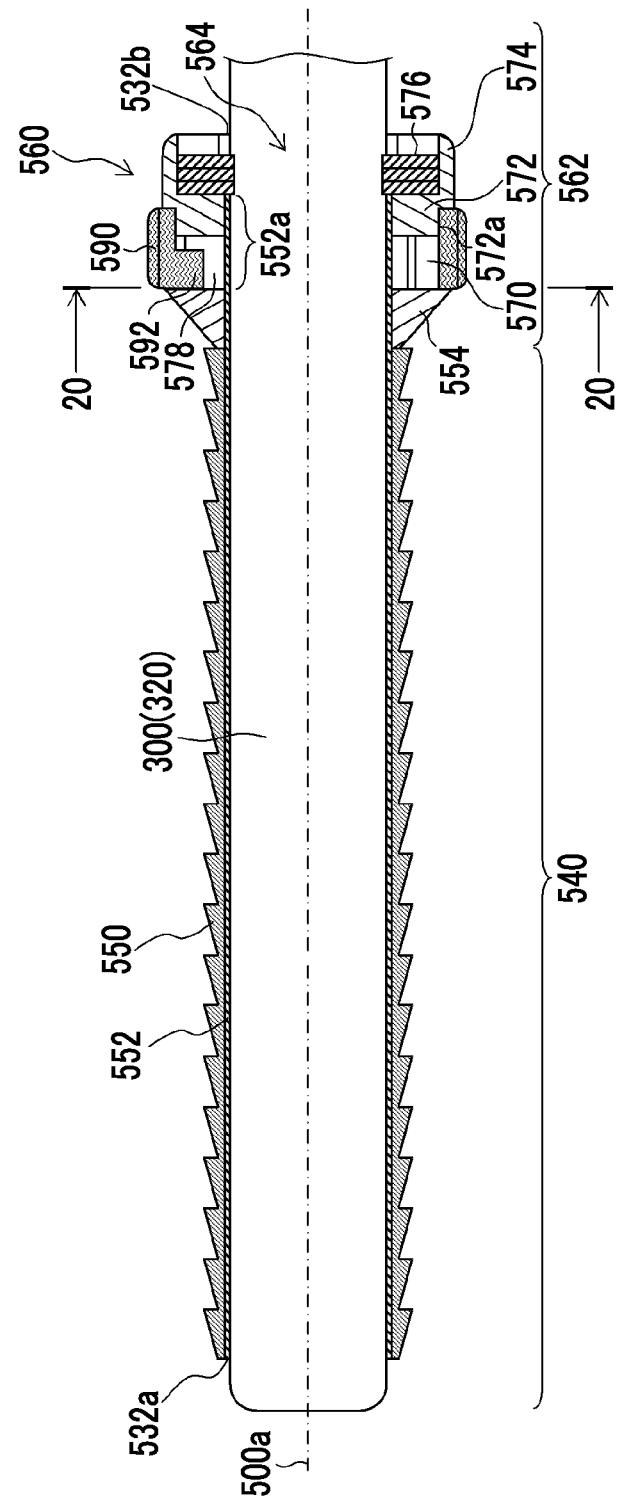
FIG. 18 is a sectional view obtained by cutting the sheathing tube along a reference axis.
Figure 19:
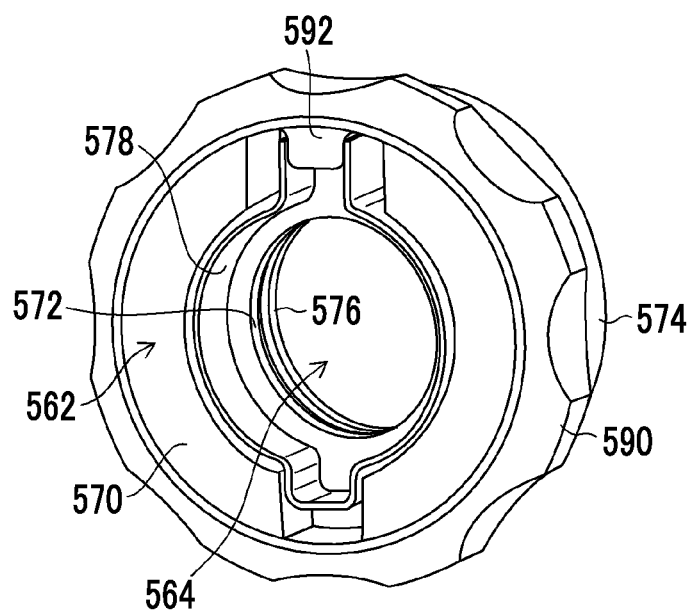
FIG. 19 is a perspective view illustrating a head part of a second cylindrical member of the sheathing tube.

FIG. 18 is a sectional view obtained by cutting the outer port 500 along the reference axis 500a, and FIG. 19 is a perspective view illustrating only the head part 560.

As illustrated in these drawings, the head part 560 includes a head body 562 to which components of the head part 560 are assembled.

The head body 562 is a cylindrical member having a through-hole 564 for allowing the overtube body 320 to be inserted therethrough, and is formed by a spring member arrangement part 570, a locking part 572, and a pressure-contact member arrangement part 574.

The locking part 572 has a smaller internal diameter than the spring member arrangement part 570 and the pressure-contact member arrangement part 574, and the internal diameter thereof substantially coincides with the external diameter of the head attachment part 552a (inner tube 552).

An annular locking projection 552b that protrudes toward the outside is formed at a base end of an outer peripheral surface of the head attachment part 552a, and the locking projection 552b is engaged with a base end (the surface of the locking part 572 on the base end side) of the locking part 572 of the head body 562. Accordingly, the head body 562 is mounted on the head attachment part 552a so as to be rotatable in a direction around the reference axis 500a without slipping out of the head attachment part 552a. Additionally, since a distal end surface (a distal end surface of the spring member arrangement part 570) of the head body 562 abuts against the surface of the flange part 554 on the base end side as illustrated in FIG. 18, the movement of the head body 562 in the axial direction with respect to the head attachment part 552a is restricted.

In the head body 562, the pressure-contact member arrangement part 574 continuously provided on the base end side of the locking part 572 has a larger internal diameter than the locking part 572 and the spring member arrangement part 570, and has the cylindrical pressure-contact member 576 (rotation restriction means) anchored to an inner peripheral surface thereof The pressure-contact member 576 is formed of elastic materials, such as elastic rubber, and the internal diameter thereof is slightly smaller than the external diameter of the overtube body 320. Therefore, when the outer port 500 is fitted to the overtube body 320, the pressure-contact member 576 is brought into pressure contact with the outer peripheral surface of the overtube body 320, and thereby, the outer port 500 is fixed to the overtube body 320. That is, the rotation and forward and backward movement of the overtube body 320 with respect to the outer port 500 are restricted by the pressure-contact member 576.

However, since the fixation herein is based on the elastic force of the pressure-contact member 576, a position where the outer port 500 is fixed to the overtube body 320 can be arbitrarily adjusted, and the outer port 500 can also be rotated relative to the overtube body 320 in the direction around the reference axis 300a (reference axis 500a). However, since the fixation using the elastic force of the pressure-contact member 576 aims at fixing the overtube body 320 to the outer port 500, power (a certain degree of force) is required for adjusting the rotation.

The spring member arrangement part 570 continuously provided on the distal end side of the locking part 572 in the head body 562 having a larger internal diameter than the locking part 572, and the internal diameter thereof is smaller than the pressure-contact member arrangement part 574.

A plate-shaped spring member 578 bent in a C shape, that is, a C-shaped spring member that has a cutout part (corresponding to the following opening 584) formed in a portion thereof in a circumferential direction is arranged inside the spring member arrangement part 570.

Figure 20:
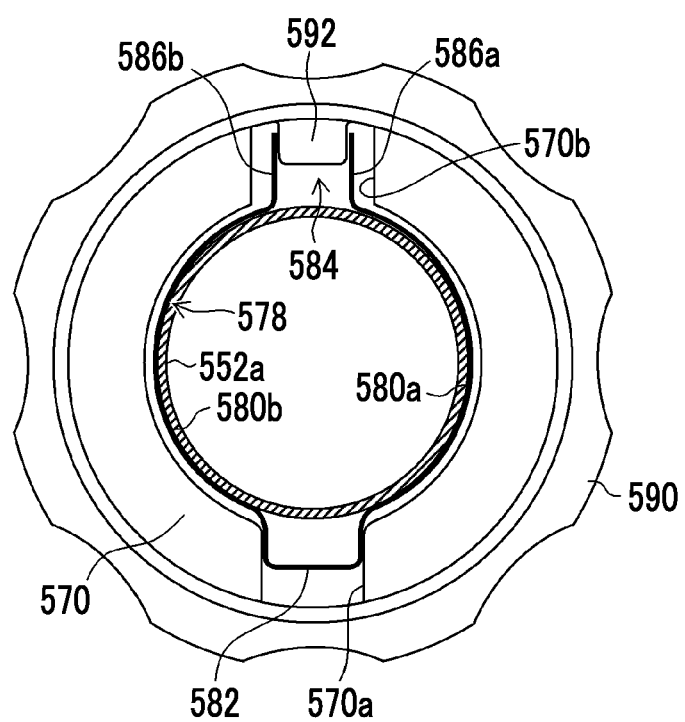
FIG. 20 is a sectional view when viewed from arrow 20-20 in FIG. 18.

To make a description on the basis of a shape on FIG. 20 that is a sectional view when viewed from arrow 20-20 in FIG. 18, the spring member 578 has a pair of pinching parts 580a and 580b that is bent in a shape along a circle (the outer peripheral surface of the head attachment part 552a) centered on the reference axis 500a, a projection part 582 that protrudes in a rectangular shape toward the outside with respect to the pinching parts 580a and 580b, and an opening 584 that is formed 180 degrees opposite to the projection part 582. Two locking pieces 586a and 586b that is formed to be bent to the outside at about 90 degrees from both ends of the pinching parts 580a and 580b is arranged in the opening 584 to face each other.

The spring member 578 has a restoring force in directions in which the opening 584 is closed, that is, directions in which the mutually facing locking pieces 586a and 586b abut against each other.

Meanwhile, an engaging groove 570a to which the projection part 582 of the spring member 578 is fitted, and an insertion groove 570b into which the locking pieces 586a and 586b are inserted are formed by notching along in the direction of the reference axis 500a, in the spring member arrangement part 570 of the head body 562.

By fitting and fixing the projection part 582 to the engaging groove 570a, the spring member 578 is held by the spring member arrangement part 570 in a state where the rotation thereof is restricted.

Additionally, the pinching parts 580a and 580b of the spring member 578 are arranged with gaps with respect to an inner peripheral surface of the spring member arrangement part 570, and the locking pieces 586a and 586b of the spring member 578 are arranged to be inserted into the insertion groove 570b of the spring member arrangement part 570, and is arranged with gaps in a wall surface of the insertion groove 570b.

Moreover, in a state where the head part 560 is mounted on the head attachment part 552a, the pinching parts 580a and 580b of the spring member 578 are brought into pressure contact with the outer peripheral surface of the head attachment part 552a and pinches the head attachment part 552a.

The spring member 578 and the head attachment part 552a are frictionally engaged with each other by a large frictional force, and the rotation of the head part 560 around the axis (around the reference axis 500a) with respect to the head attachment part 552a is restricted. That is, a state (rotation locked state) where the rotation of the head part 560 around the axis with respect to the sheathing tube insertion part 540 in the outer port 500 is locked is brought about. In a case where the outer port 500 is fitted to the overtube 300, the rotation of the overtube 300 around the axis with respect to the sheathing tube insertion part 540 of the outer port 500 is also restricted together with the rotation locked state of the head part 560.

Meanwhile, a cylindrical rotation operating member 590 is supported on an outer peripheral surface of the spring member arrangement part 570 so as to be slidable in a circumferential direction. As illustrated in FIG. 18, the rotation operating member 590 reaches a partial range of the locking part 572, and an outer peripheral surface 572a on the distal end side having a smaller diameter than on the base end side and having almost the same diameter as an outer peripheral surface of the spring member arrangement part 570 is formed on an outer peripheral surface of the locking part 572. The rotation operating member 590 is supported also in the outer peripheral surface 572a so as to be slidable in the circumferential direction.

Additionally, the rotation operating member 590 slidably abuts against a step of the outer peripheral surface 572a of the locking part 572 on the base end side and the surface of the flange part 554 on the base end side, and the movement thereof in the direction of the reference axis 500a is restricted.

An engaging projection 592 (locking part) protrudes in a rectangular shape toward the inside is formed on an inner peripheral surface of the rotation operating member 590. The engaging projection 592 is formed within a range of the spring member arrangement part 570 of the rotation operating member 590, and as illustrated in FIG. 20, is arranged to be inserted into the insertion groove 570b.

Additionally, the engaging projection 592 of the rotation operating member 590 is arranged within the insertion groove 570b with a gap between the two locking pieces 586a and 586b in the opening 584 of the spring member 578.

Figure 21:
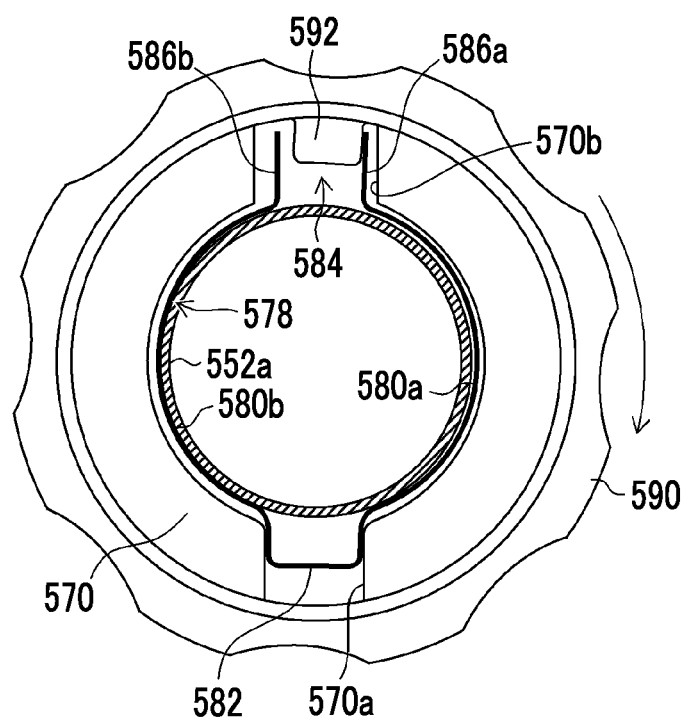
FIG. 21 is a sectional view illustrating an aspect when a rotation operating member is rotated in a clockwise direction in FIG. 20.

Therefore, if the rotation operating member 590 is rotated in any direction (for example, the clockwise direction in FIG. 20) around the axis, as illustrated in FIG. 21, the engaging projection 592 abuts against a locking piece (the locking piece 586a in FIG. 21) arranged in the rotational direction out of the locking piece 586a and the locking pieces 586b, and moves the locking piece, and the width (opening width) of the opening 584 is expanded.

Accordingly, the pinching of the head attachment part 552a by the pinching parts 580a and 580b of the spring member 578 is released. Then, the frictional engagement between the spring member 578 and the head attachment part 552a is released, and the rotation of the head part 560 around the axis (around the reference axis 500a) with respect to the head attachment part 552a is allowed. That is, a state (rotation unlocked state) where the rotation of the head part 560 around the axis with respect to the sheathing tube insertion part 540 in the outer port 500 is unlocked is brought about.

Additionally, as one transmission path, the rotational operation force of the rotation operating member 590 is transmitted from the engaging projection 592 via the spring member 578 to the projection part 582 and is transmitted from the projection part 582 through the wall surface of the engaging groove 570a to the spring member arrangement part 570, and thereby is transmitted to a head body 562 having the spring member arrangement part 570 as a portion. Additionally, as another transmission path, the rotational operation force of the rotation operating member 590 is transmitted to the spring member arrangement part 570 and transmitted to the head body 562 when the engaging projection 592 abutting against the wall surface of the insertion groove 570b or the width of the opening 584 is expanded by the engaging projection 592, and thereby, the locking piece 586a or the locking piece 586b comes into contact with the inner peripheral surface of the spring member arrangement part 570.

Therefore, substantially simultaneously with the head part 560 being switched from the rotation locked state to the rotation unlocked state, the head part 560 rotates in the rotational direction of the rotation operating member 590 with respect to the head attachment part 552a, that is, with respect to the sheathing tube insertion part 540 of the outer port 500.

In this case, in a case where the outer port 500 is fitted to the overtube 300, the overtube 300 also rotates in the rotational direction of the rotation operating member 590 with respect to the sheathing tube insertion part 540 of the outer port 500 together with the rotation of the head part 560.

According to this, when the rotation operating member 590 of the outer port 500 is not operated in a state where the overtube 300 to which the outer port 500 is fitted is inserted into a body wall, the head part 560 is brought into the rotation locked state, and thereby, unintended rotation of the overtube 300 around the axis is prevented.

Meanwhile, in a case where the positional relationship between the endoscope insertion part 102 and the treatment tool insertion part 202 inserted through the overtube 300 is to be inserted by changing the rotational angle of the overtube 300 around the axis, if the rotation operating member 590 of the outer port 500 is rotationally operated in a direction in which the overtube 300 is to be rotated, the head part 560 can be switched to the rotation unlocked state, and the overtube 300 can be rotated together with the head part 560 in the direction of the rotational operation.

Figure 22A:
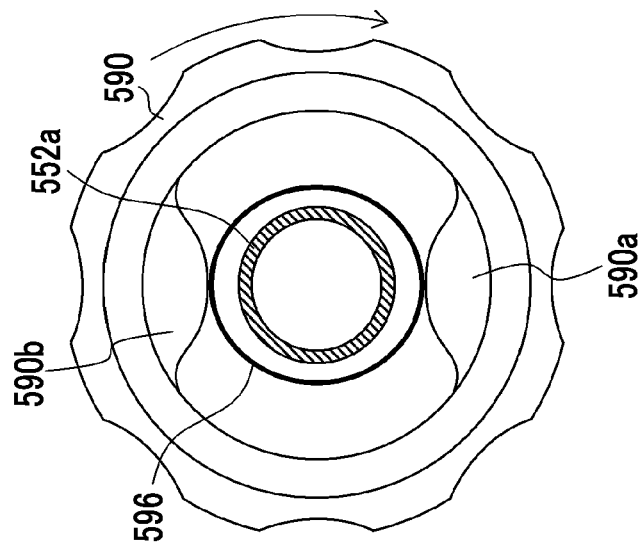
FIGS. 22A and 22B are views illustrating another embodiment of a switching mechanism that switches between a rotation locked state and a rotation unlocked state of the second cylindrical member of the sheathing tube.
Figure 22B:
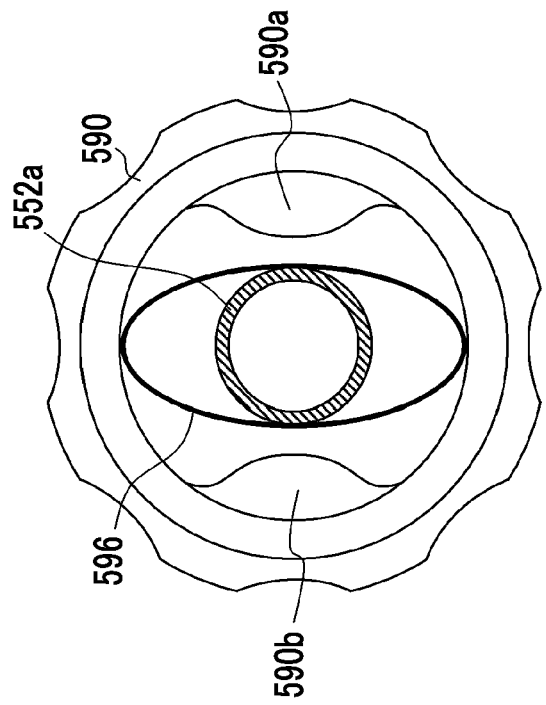

As described above, in the above embodiment, regarding the switching mechanism for the rotation locked state and the rotation unlocked state of the head part 560 with respect to the sheathing tube insertion part 540 of the outer port 500, a mechanism that validly or invalidly switches the frictional engagement of the C-shaped spring member 578 with the head attachment part 552a depending on the presence/absence of the rotational operation of the rotation operating member 590 is adopted. However, the invention is not limited to this, for example, an elliptical spring member 596 as illustrated in FIG. 22A may be used instead of the C-shaped spring member 578. In the state of FIG. 22A, the head part 560 is set to the rotation locked state when the elliptical spring member 596 pinches the head attachment part 552a in the direction of a minor axis and is frictionally engaged therewith. Meanwhile, in a case where the rotational operation of the rotation operating member 590 is performed as illustrated in FIG. 22B, the spring member 596 is pressed the direction of the major axis by protruding portions 590a and 590b, which are formed on an inner peripheral side of the rotation operating member 590, or the like, and the spring member 596 is deformed. Accordingly, the head part 560 can be brought into the rotation unlocked state by releasing the frictional engagement of the spring member with the head attachment part 552a.

Additionally, although an example in which the head part 560 is externally fitted to the base end of the sheathing tube insertion part 540 has been described in the above embodiment, the head part 560 is not necessarily externally fitted to the sheathing tube insertion part 540. For example, a portion of the spring member on the distal end side may be externally fitted to the base end of the sheathing tube insertion part 540, and a portion of the spring member on the base end side may be fitted to the head part. Moreover, the sheathing tube insertion part 540 and the head part 560 may be engaged with each other when the spring member applies a pressing force to the base end of the sheathing tube insertion part 540 from the longitudinal axis.

Additionally, although a case where the invention is applied to the outer port 500 that prevents the rotation of the overtube 300 around the axis with respect to a body wall and the forward and backward movement thereof in the axial direction has been described in the above embodiment, the invention can also be applied to sheathing tubes sheathing other tubular members other than the overtube 300.

That is, the invention can also be applied to a sheathing tube including a first cylindrical member having a distal end opening from which a tubular member is delivered, a second cylindrical member that is rotatably coupled to a base end of the first cylindrical member and has a base end opening into which a tubular member is introduced, and rotation restriction means that is provided in the second cylindrical member and restricts the rotation of the tubular member with respect to the second cylindrical member. The invention can also be applied to between the overtube 300 and the endoscope 100 if necessary.

Additionally, the tubular member having the sheathing tube to which the invention is applied sheathed thereto is not limited to the overtube 300 illustrated in the above embodiment. For example, the tubular member may be an overtube that does not include the interlocking function (slider 400), may be an overtube only including the endoscope insertion passage or the treatment tool insertion passage through which the endoscope insertion part is inserted, or may be tubular members used for other applications without being limited to the overtube that guides an insertion part of a medical instrument to be inserted into a body cavity into the body cavity.

EXPLANATION OF REFERENCES

10: endoscopic surgical device
100: endoscope
102: endoscope insertion part
200: treatment tool
202: treatment tool insertion part
300: overtube
300a, 500a: reference axis
306: endoscope insertion passage
306a: endoscope insertion axis
308: treatment tool insertion passage
308a: treatment tool insertion axis
320: overtube body
340: base end cap
360: distal end cap
400: slider
576: pressure-contact member
500: outer port
540: insertion part
542: base end
552: inner tube
552a: head attachment part
554: flange part
560: head part
562: head body
570: spring member arrangement part
572: locking part
574: pressure-contact member arrangement part
578: spring member
580a, 580b: pinching member
582: projection part
584: opening
586a, 586b: locking piece
590: rotation operating member
592: engaging projection

What is claimed is:
1. A sheathing tube configured to sheath a tubular member, the sheathing tube comprising:
   a first cylindrical member having a distal end opening from which the tubular member is delivered;
   a second cylindrical member that is rotatably connected to a base end of the first cylindrical member and has a base end opening configured for introduction of the tubular member;
   a rotation restriction part that is provided in an inner peripheral surface of the second cylindrical member and restricts rotation of the tubular member with respect to the second cylindrical member by having an internal diameter smaller than an external diameter of the tubular member;
   a spring member that is arranged between the first cylindrical member and the second cylindrical member and is deformable between a rotation locked state where rotation of the second cylindrical member with respect to the first cylindrical member is restricted by engagement of the spring member with the base end of the first cylindrical member, and a rotation unlocked state where the engagement is released and the rotation of the second cylindrical member with respect to the first cylindrical member is allowed; and
   a rotation operating member that is rotatably provided in an axial direction of the second cylindrical member and supported on an outer peripheral surface of the spring member, abuts against a step of an outer peripheral surface of the second cylindrical member, and deforms the spring member between the rotation locked state and the rotation unlocked state by sliding along the outer peripheral surface of the spring member in a circumferential direction, wherein an internal diameter of a distal end of the second cylindrical member is larger than an external diameter of the base end of the first cylindrical member, and the distal end of the second cylindrical member is arranged so as to cover the base end of the first cylindrical member, and wherein the spring member is arranged between the distal end of the second cylindrical member and the base end of the first cylindrical member.

2. The sheathing tube according to claim 1, wherein the spring member includes a C-shaped spring member having a cutout part formed in a portion thereof in a circumferential direction, wherein the spring member includes a projection part protruding toward outside in a radial direction, and the projection part is engaged with an engaging groove provided inside the second cylindrical member, and thereby, rotation of the spring member with respect to the second cylindrical member is restricted, and wherein the rotation operating member includes a locking part locked in the cutout part, and in a case where the rotation operating member is rotationally operated, the spring member is deformed from the rotation locked state to the rotation unlocked state by expanding an opening width of the cutout part in a state where the locking part is locked in the cutout part.

3. The sheathing tube according to claim 1, wherein the tubular member is an overtube that guides an insertion part of a medical instrument to be inserted into a body cavity into the body cavity.

4. An endoscopic surgical device comprising:

an overtube that guides an insertion part of a medical instrument to be inserted into a body cavity into the body cavity; and a sheathing tube sheathing the overtube, wherein the sheathing tube includes a first cylindrical member having a distal end opening from which the overtube is delivered, a second cylindrical member that is rotatably connected to a base end of the first cylindrical member and has a base end opening into which the overtube is introduced, a rotation restriction part that is provided in an inner peripheral surface of the second cylindrical member and restricts rotation of the overtube with respect to the second cylindrical member by having an internal diameter smaller than an external diameter of the overtube, a spring member that is disposed between the first cylindrical member and the second cylindrical member and is deformable between a rotation locked state where rotation of the second cylindrical member with respect to the first cylindrical member is restricted by engagement of the spring member with the base end of the first cylindrical member, and a rotation unlocked state where the engagement is released and the rotation of the second cylindrical member with respect to the first cylindrical member is allowed, and a rotation operating member that is rotatably provided in an axial direction of the second cylindrical member and supported on an outer peripheral surface of the spring member, abuts against a step of an outer peripheral surface of the second cylindrical member, and deforms the spring member between the rotation locked state and the rotation unlocked state by sliding along the outer peripheral surface of the spring member in a circumferential direction, wherein an internal diameter of a distal end of the second cylindrical member is larger than an external diameter of the base end of the first cylindrical member, and the distal end of the second cylindrical member is arranged so as to cover the base end of the first cylindrical member, and wherein the spring member is arranged between the distal end of the second cylindrical member and the base end of the first cylindrical member.

* * * * *